(12) United States Patent
Onishi

(10) Patent No.: US 11,193,113 B2
(45) Date of Patent: Dec. 7, 2021

(54) TRANSGENIC YEAST AND METHOD FOR PRODUCING ETHANOL USING THE SAME

(71) Applicant: TOYOTA JIDOSHA KABUSHIKI KAISHA, Toyota (JP)

(72) Inventor: Toru Onishi, Toyota (JP)

(73) Assignee: TOYOTA JIDOSHA KABUSHIKI KAISHA, Toyota (JP)

(*) Notice: Subject to any disclaimer, the term of this patent is extended or adjusted under 35 U.S.C. 154(b) by 0 days.

(21) Appl. No.: 16/592,181

(22) Filed: Oct. 3, 2019

(65) Prior Publication Data

US 2020/0109373 A1    Apr. 9, 2020

(30) Foreign Application Priority Data

Oct. 5, 2018 (JP) .............................. JP2018-189621

(51) Int. Cl.
| C12N 1/15 | (2006.01) |
| C12N 1/19 | (2006.01) |
| C12N 9/04 | (2006.01) |
| C12P 7/06 | (2006.01) |
| C12N 1/16 | (2006.01) |
| C12P 7/10 | (2006.01) |

(52) U.S. Cl.
CPC ............. C12N 9/0006 (2013.01); C12N 1/16 (2013.01); C12P 7/10 (2013.01); C12Y 101/01006 (2013.01)

(58) Field of Classification Search
None
See application file for complete search history.

(56) References Cited

U.S. PATENT DOCUMENTS 6,333,181 B1 * 12/2001 Ingram ................... C12N 13/00
                                                      435/165
8,445,243 B2    5/2013 Matsushika et al.
8,772,012 B2    7/2014 Katahira et al.
2010/0192985 A1 * 8/2010 Aehle ................ C11D 3/38645
                                                      134/26
2011/0294170 A1 * 12/2011 Subbian .................... C12P 7/04
                                                      435/106

FOREIGN PATENT DOCUMENTS

| JP | 2009-195220 A | 9/2009 |
| JP | 2011-147445 A | 8/2011 |
| WO | 2007/099451 A1 | 9/2007 |
| WO | 2007/106524 A2 | 9/2007 |
| WO | 2012067510 A1 | 5/2012 |
| WO | 2013081456 A2 | 6/2013 |
| WO | 2014074895 A2 | 5/2014 |
| WO | 2015028582 A2 | 3/2015 |
| WO | 2018/114762 A1 | 6/2018 |
| WO | 2019/063507 A1 | 4/2019 |

OTHER PUBLICATIONS

Zhang et al., Structure 26:1474-1485, 2018 (Year: 2018).*
UniProt Database Accession No. 013702, 2017, 3 pages (Year: 2017).*
Solomon et al., Met. Eng. Commun. 3:68-75, 2016 (Year: 2016).*
Matsuzawa et al., Appl. Microbiol. Biotechnol. 87:715-727, 2010 (Year: 2010).*
Gong et al., Biotechnol. Bioengineer. vol. XXV, pp. 85-102, 1983 (Year: 1983).*
Wen-Tao Ding et al., "3' Truncation of the GPD1 Promoter in *Saccharomyces cerevisiae* for Improved Ethanol Yield and Productivity", Applied and Environmental Microbiology, 2013, pp. 3273-3281, vol. 79.
Kyung Ok Yu et al., "Engineering of glycerol utilization pathway for ethanol production by *Saccharomyces cerevisiae*", Bioresource Technology, 2010, pp. 4157-4161, vol. 101.

* cited by examiner

*Primary Examiner* — David Steadman
(74) *Attorney, Agent, or Firm* — Sughrue Mion, PLLC

(57) ABSTRACT

The present disclosure is intended to reduce the amount of glycerin produced as a by-product in ethanol fermentation to a significant extent using a transgenic yeast comprising a gene having the pentose assimilating ability and encoding glycerin dehydrogenase having a mitochondrial transport signal introduced thereinto.

11 Claims, No Drawings

Specification includes a Sequence Listing.

TRANSGENIC YEAST AND METHOD FOR PRODUCING ETHANOL USING THE SAME

CROSS REFERENCE TO RELATED APPLICATIONS

The present application claims priority from Japanese patent application JP 2018-189621 filed on Oct. 5, 2018, the content of which is hereby incorporated by reference into this application.

BACKGROUND

Technical Field

The present disclosure relates to a transgenic yeast capable of metabolizing pentose, such as xylose, and a method for producing ethanol using the same.

Background Art

A cellulosic biomass is an effective starting material for a useful alcohol, such as ethanol, or an organic acid. In order to increase the amount of ethanol produced with the use of a cellulosic biomass, yeasts capable of utilizing xylose, which is pentose, as a substrate have been developed. For example, JP 2009-195220 A discloses a transgenic yeast resulting from incorporation of a xylose reductase (XR) gene and a xylitol dehydrogenase (XDH) gene derived from *Pichia stipitis* into its chromosome. Also, a report has been made concerning a xylose-assimilating yeast into which a xylose isomerase (XI) gene (derived from the intestinal protozoa of termites) has been introduced (JP 2011-147445 A). When both XR and XDH are introduced or when XI is introduced, xylulose is generated in the xylose-assimilating pathway, and xylulose is converted into xylulose 5-phosphate with the aid of xylulokinase. Xylulose 5-phosphate is metabolized in the pentose phosphate pathway and is then converted into glyceraldehyde-3-phosphate. Glyceraldehyde-3-phosphate enters the glycolytic pathway and ethanol is generated in the end.

Glycerin is a representative by-product of ethanol production. In order to increase an ethanol yield, accordingly, it is critical to reduce the amount of glycerin. In yeasts, glycerin is biosynthesized from dihydroxyacetone phosphate (DHAP), which is an intermediate product of the glycolysis system, through glycerin 3 phosphate. By lowering activity of glycerin 3 phosphate dehydrogenase, which is a major enzyme in the glycerin production pathway, the amount of glycerin production can be reduced. Because activity of such enzyme are highly correlated with growth and the ethanol production speed (Ding, W. T., et al., Apple Environ. Microbiol., 79, 2013, 3273-3281; FIG. 3), a strain with lowered glycerin 3 phosphate dehydrogenase activity is problematic in terms of productivity of ethanol.

Alternatively, the amount of glycerin production can be reduced by a method comprising metabolizing glycerin to convert into ethanol. In the past, there was a report concerning a method comprising overexpressing the gene associated with the glycerin metabolic pathway endogenous in *Saccharomyces cerevisiae* wherein glycerin assimilation is accelerated (Yu, K. O., et al., Bioresour. Technol., 101, 2010, 4157). While the endogenous glycerin metabolic pathway reduces NADP, the glycerin production pathway oxidizes NADH. In a series of reactions involving glycerin production and metabolism, accordingly, redox imbalance occurs. In order to overcome such drawbacks, accordingly, a technique involving introducing the glycerin metabolic pathway derived from NAD-reducing bacteria so as to balance NAD and NADH used for glycerin production and metabolism and accelerate the glycerin metabolism was reported (WO 2013/081456).

SUMMARY

Effects of reducing the amount of glycerin production attained by the technique aimed at accelerating glycerin metabolism as described above were insufficient. Accordingly, a technique of further reducing the amount of glycerin produced as a by-product in ethanol fermentation has been expected.

Under the above circumstances, the present disclosure provides a transgenic yeast producing a significantly small amount of glycerin, which is a by-product in ethanol fermentation, and a method of ethanol production using such transgenic yeast.

To this end, we have conducted concentrated studies and discovered that a transgenic yeast into which a gene encoding glycerin dehydrogenase having a mitochondrial transport signal has been introduced would exhibit a smaller amount of glycerin production, compared with a yeast into which no such gene had been introduced. This has led to the completion of the technique of the present disclosure.

The present disclosure encompasses the following.

(1) A transgenic yeast having pentose assimilating ability, comprising a gene encoding glycerin dehydrogenase having a mitochondrial transport signal introduced thereinto.

(2) The transgenic yeast according to (1), wherein the glycerin dehydrogenase is NAD-dependent glycerin dehydrogenase having activity of converting NAD into NADPH.

(3) The transgenic yeast according to (1), wherein the gene encoding glycerin dehydrogenase encodes the protein (a) or (b):

(a) a protein comprising the amino acid sequence as shown in SEQ ID NO: 2; or (b) a protein comprising an amino acid sequence having 70% or higher sequence identity to the amino acid sequence as shown in SEQ ID NO: 2, having mitochondrial locality, and having activity of generating dihydroxyacetone using glycerin as a substrate.

(4) The transgenic yeast according to (1), wherein the gene encoding glycerin dehydrogenase encodes a fusion protein comprising a mitochondrial transport signal and the protein (a) or (b):

(a) a protein comprising the amino acid sequence as shown in SEQ ID NO: 4; or (b) a protein comprising an amino acid sequence having 70% or higher sequence identity to the amino acid sequence as shown in SEQ ID NO: 4, and having activity of generating dihydroxyacetone using glycerin as a substrate.

(5) The transgenic yeast according to (1), wherein the pentose is xylose and/or arabinose.

(6) The transgenic yeast according to (1), which comprises the xylose isomerase gene introduced thereinto and has xylose assimilating ability.

(7) The transgenic yeast according to (6), which further comprises a xylulokinase gene introduced thereinto.

(8) The transgenic yeast according to (1), which comprises a gene encoding an enzyme selected from a group of enzymes constituting a non-oxidative process in the pentose phosphate pathway introduced thereinto.

(9) The transgenic yeast according to (8), wherein the group of enzymes constituting a non-oxidative process in the pentose phosphate pathway includes ribose-5-phosphate isomerase, ribulose-5-phosphate-3-epimerase, transketolase, and transaldolase.

(10) A method for producing ethanol comprising a step of ethanol fermentation by culturing the transgenic yeast according to any of (1) to (9) in a medium containing assimilable pentose.

(11) The method for producing ethanol according to (10), wherein the medium contains cellulose and the ethanol fermentation proceeds simultaneously at least with cellulose saccharification.

Effects

In comparison with a transgenic yeast comprising a cytoplasm-localized glycerin dehydrogenase gene introduced thereinto, the transgenic yeast of the present disclosure has glycerin metabolizing ability improved to a significant extent. With the use of the transgenic yeast of the present disclosure, more specifically, the amount of glycerin produced as a by-product in ethanol fermentation can be reduced to a significant extent, and an excellent ethanol yield can be achieved.

DETAILED DESCRIPTION

Hereafter, the present disclosure is described in greater detail with reference to the embodiments.

[Transgenic Yeast]

The transgenic yeast of the present disclosure has pentose assimilating ability and comprises a gene encoding glycerin dehydrogenase having a mitochondrial transport signal introduced thereinto. The term "pentose assimilating ability" used herein refers to pentose assimilating ability achieved by introducing an enzyme gene involving pentose assimilation into a yeast that does not inherently have pentose assimilating ability (synonymous with "metabolizing ability"), and the term also refers to an inherent pentose assimilating ability because of the presence of an enzyme gene associated with pentose assimilation. More specifically, the term "pentose" refers to aldopentose, such as ribose, arabinose, xylose, or lyxose, and ketopentose, such as ribulose or xylulose, although pentose is not particularly limited thereto. In some embodiments, the transgenic yeast of the present disclosure may have xylose and/or arabinose assimilating ability among various types of pentoses. In more specific embodiments, the transgenic yeast may have xylose assimilating ability.

Examples of yeasts having xylose assimilating ability include a yeast that has acquired xylose assimilating ability by introduction of the xylose isomerase gene into a yeast that does not inherently have xylose assimilating ability and a yeast that has acquired xylose assimilating ability by introduction of another gene involving xylose assimilation. Examples of yeasts having the arabinose-assimilating ability include yeasts that have each acquired the arabinose-assimilating ability by introduction of an L-arabinose isomerase gene, an L-ribulokinase gene, and an L-ribulose-5-phosphate-4-epimerase gene derived from prokaryotes and an L-arabitol-4-dehydrogenase gene and an L-xylose reductase gene derived from eukaryotes into a yeast that does not inherently have the arabinose-assimilating ability.

[Glycerin Dehydrogenase Gene]

The transgenic yeast of the present disclosure comprises a gene encoding glycerin dehydrogenase having a mitochondrial transport signal. A glycerin dehydrogenase gene to be introduced into a host yeast may be a gene encoding mitochondria-localized glycerin dehydrogenase or a gene encoding a fusion protein comprising cytoplasm-localized glycerin dehydrogenase and a mitochondrial transport signal fused thereto. Specifically, a gene encoding mitochondria-localized glycerin dehydrogenase inherently has a mitochondrial transport signal.

In some embodiments, mitochondria-localized glycerin dehydrogenase and cytoplasm-localized glycerin dehydrogenase in the transgenic yeast of the present disclosure may be NAD-dependent glycerin dehydrogenase. The NAD-dependent glycerin dehydrogenase reduces NAD (NAD→NADH) as a coenzyme in a reaction of generating dihydroxyacetone using glycerin as a substrate. A glycerin production pathway oxidizes NADH. Hence, this makes balance between coenzymes in a series of reactions involving glycerin production and metabolism since.

Examples of genes encoding mitochondria-localized glycerin dehydrogenase include the gld1 gene of the fission yeast, *Schizosaccharomyces pombe* (NAD-dependent), and the Gld1 gene of the fission yeast, *Schizosaccharomyces octosporus* (NAD-dependent) (NCBI Accession Number: XP_013020646). In addition, amino acid sequences of mitochondrial transport signals can be easily inspected with the use of protein subcellular localization prediction tools, such as TargetP (cbs.dtu.dk/services/TargetP/).

Specifically, the nucleotide sequence of the coding region in the *Schizosaccharomyces pombe* gld1 gene is shown in SEQ ID NO: 1, and the amino acid sequence of the gld1 protein (with a mitochondrial transport signal) is shown in SEQ ID NO: 2. The gene encoding glycerin dehydrogenase having a mitochondrial transport signal is not limited to the gld1 gene identified by SEQ ID NO: 1 and SEQ ID NO: 2, and it may be a paralogous gene or a homologous gene of the gld1 gene in the narrow sense having different nucleotide and amino acid sequences.

The gene encoding glycerin dehydrogenase is not limited to the gene identified by SEQ ID NO: 1 and SEQ ID NO: 2. For example, it may be a gene encoding a protein comprising an amino acid sequence having 70% or higher sequence similarity to or identity with the amino acid sequence as shown in SEQ ID NO: 2 and having activity of generating dihydroxyacetone using glycerin as a substrate by being localized in the mitochondria. In some embodiments, such sequence similarity or identity may be 80% or higher, 90% or higher, or 95% or higher. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the gene encoding glycerin dehydrogenase is not limited to the gene identified by SEQ ID NO: 1 and SEQ ID NO: 2. For example, it may be a gene encoding a protein comprising an amino acid sequence derived from the amino acid sequence as shown in SEQ ID NO: 2 by substitution, deletion, insertion, or addition of one or several amino acids and and having activity of generating dihydroxyacetone using glycerin as a substrate by being localized in the mitochondria. The term "several" used herein refers to, for example, 2 to 30. In some embodiments, it may refer to 2 to 20, 2 to 10, or 2 to 5.

Furthermore, the gene encoding glycerin dehydrogenase is not limited to the gene identified by SEQ ID NO: 1 and SEQ ID NO: 2. For example, it may be a gene hybridizing under stringent conditions to the full-length sequence or a partial sequence of a complementary strand of DNA comprising the nucleotide sequence as shown in SEQ ID NO: 1 and encoding a protein having activity of generating dihydroxyacetone using glycerin as a substrate by being localized in the mitochondria. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM. In some embodiments, the sodium concentration may be 25 to 300 mM. The temperature is 42° C. to 68° C. In some embodiments, the temperature may be 42° C. to 65° C. Further specifically, the sodium concentration is 5×SSC (83 mM NaCl, 83 mM sodium citrate), and the temperature is 42° C.

Examples of genes encoding cytoplasm-localized glycerin dehydrogenase include the gldA gene derived from *Escherichia coli* (NAD-dependent) and the gldA gene derived from *Klebsiella pneumoniae* and *Thermoanaerobacterium thermosaccharolyticum*. A majority of NAD-dependent glycerin dehydrogenase is derived from prokaryotes and is localized in the cytoplasm.

Specifically, the nucleotide sequence of the coding region in the gldA gene derived from *E. coli* is shown in SEQ ID NO: 3, and the amino acid sequence of the gldA protein (without a mitochondrial transport signal) is shown in SEQ ID NO: 4. The gene encoding cytoplasm-localized glycerin dehydrogenase is not limited to the gldA gene identified by SEQ ID NO: 3 and SEQ ID NO: 4, and it may be a paralogous gene or a homologous gene of the gldA gene in the narrow sense having different nucleotide and amino acid sequences.

The gene encoding glycerin dehydrogenase is not limited to the gene identified by SEQ ID NO: 3 and SEQ ID NO: 4. For example, it may be a gene encoding a protein comprising an amino acid sequence having 70% or higher sequence similarity to or identity with the amino acid sequence as shown in SEQ ID NO: 4 and having activity of generating dihydroxyacetone using glycerin as a substrate. In some embodiments, such sequence similarity or identity may be 80% or higher, 90% or higher, or 95% or higher. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the gene encoding glycerin dehydrogenase is not limited to the gene identified by SEQ ID NO: 3 and SEQ ID NO: 4. For example, it may be a gene encoding a protein comprising an amino acid sequence derived from the amino acid sequence as shown in SEQ ID NO: 4 by substitution, deletion, insertion, or addition of one or several amino acids and having activity of generating dihydroxyacetone using glycerin as a substrate. The term "several" used herein refers to, for example, 2 to 30. In some embodiments, it may refer to 2 to 20, 2 to 10, or 2 to 5.

Furthermore, the gene encoding glycerin dehydrogenase is not limited to the gene identified by SEQ ID NO: 3 and SEQ ID NO: 4. For example, it may be a gene hybridizing under stringent conditions to the full-length sequence or a partial sequence of a complementary strand of DNA comprising the nucleotide sequence as shown in SEQ ID NO: 3 and encoding a protein having activity of generating dihydroxyacetone using glycerin as a substrate. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM. In some embodiments, the sodium concentration may be 25 to 300 mM. The temperature is 42° C. to 68° C. In some embodiments, the temperature may be 42° C. to 65° C. Further specifically, the sodium concentration is 5×SSC (83 mM NaCl, 83 mM sodium citrate), and the temperature is 42° C.

A mitochondrial transport signal fused to the cytoplasm-localized glycerin dehydrogenase is not particularly limited. An example thereof is a given N-terminal region (i.e., a mitochondrial transport signal) in the mitochondria-localized glycerin dehydrogenase described above. For example, an N-terminal region may comprise 15 to 70 amino acid residues from the N terminus. In some embodiments, such region may comprise 20 to 50 amino acids or 25 to 45 amino acid residues from the N terminus. An example of a mitochondrial transport signal is a region comprising 30 amino acid residues from the N terminus of glycerin dehydrogenase (SEQ ID NO: 2) encoded by the *Schizosaccharomyces pombe* gld1 gene.

As mitochondrial transport signals, various known sequences can be used without particular limitation. Concerning a mitochondrial transport signal, a reference may be made to, for example, the EMBO Journal, vol. 5, no. 6, pp. 1335-1342, 1986. Also, protein subcellular localization prediction tools, such as TargetP (cbs.dtu.dk/services/TargetP/), may be used. This enables prediction of mitochondrial transport signals based on mitochondria-localized proteins.

As described above, whether or not a gene comprising a nucleotide sequence that differs from the nucleotide sequence as shown in SEQ ID NO: 1 or 3 or a gene encoding an amino acid sequence that differs from the amino acid sequence as shown in SEQ ID NO: 2 or 4 would function as a glycerin dehydrogenase gene may be determined by, for example, preparing an expression vector comprising the gene of interest incorporated into an adequate site between a promoter and a terminator, transforming an *E. coli* host using such expression vector, and assaying the glycerin dehydrogenase activity of the protein expressed. The term "glycerin dehydrogenase activity" refers to activity of generating dihydroxyacetone using glycerin as a substrate. Accordingly, glycerin dehydrogenase activity can be evaluated by preparing a solution containing glycerin as a substrate, allowing the target protein to react at an adequate temperature, and measuring the amount of glycerin that has decreased and/or the amount of dihydroxyacetone that has been generated.

[Xylose Metabolism-Associated Gene]

The transgenic yeast of the present disclosure may have ability of assimilating, for example, xylose among various types of pentoses (i.e., the xylose assimilating ability). Specifically, it can assimilate xylose contained in a medium to generate ethanol. Xylose contained in a medium may be obtained by saccharification of xylan or hemicellulose comprising xylose as a constituent saccharide. Alternatively, it may be supplied to a medium as a result of saccharification of xylan or hemicellulose contained in a medium by a saccharifying enzyme. The latter case refers to the so-called simultaneous saccharification and fermentation process.

Examples of yeasts having xylose-metabolizing ability include a yeast that has acquired xylose-metabolizing ability as a result of introduction of a xylose isomerase gene into a yeast that does not inherently have xylose-metabolizing ability and a yeast that has acquired xylose-assimilating ability as a result of introduction of another xylose assimilation-associated gene.

The xylose isomerase gene (the XI gene) is not particularly limited, and a gene originating from any organism species may be used. For example, a plurality of the xylose isomerase genes derived from the intestinal protozoa of termites disclosed in JP 2011-147445 A can be used without particular limitation. Examples of the xylose isomerase genes that can be used include a gene derived from the anaerobic fungus *Piromyces* sp. strain E2 (JP 2005-514951 A), a gene derived from the anaerobic fungus *Cyllamyces aberensis*, a gene derived *Clostridium phytofermentans*, and a gene derived from the *Streptomyces murinus* cluster.

Specifically, a xylose isomerase gene derived from the intestinal protozoa of *Reticulitermes speratus* may be used. The nucleotide sequence of the coding region of the xylose isomerase gene derived from the intestinal protozoa of *Reticuliterhes speratus* and the amino acid sequence of a protein encoded by such gene are shown in SEQ ID NO: 5 and SEQ ID NO: 6, respectively.

The xylose isomerase gene is not limited to the gene identified by SEQ ID NO: 5 and SEQ ID NO: 6. It may be a paralogous gene or a homologous gene in the narrow sense having different nucleotide and amino acid sequences.

The xylose isomerase gene is not limited to the gene identified by SEQ ID NO: 5 and SEQ ID NO: 6. For example, it may be a gene encoding a protein comprising an amino acid sequence having 70% or higher sequence similarity to or identity with the amino acid sequence as shown in SEQ ID NO: 6 and having xylose isomerase activity. In some embodiments, such sequence similarity or identity may be 80% or higher, 90% or higher, or 95% or higher. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the xylose isomerase gene is not limited to the gene identified by SEQ ID NO: 5 and SEQ ID NO: 6. For example, it may be a gene encoding a protein comprising an amino acid sequence derived from the amino acid sequence as shown in SEQ ID NO: 6 by substitution, deletion, insertion, or addition of one or several amino acids and having xylose isomerase activity. The term "several" used herein refers to, for example, 2 to 30. In some embodiments, it may refer to 2 to 20, 2 to 10, or 2 to 5.

Furthermore, the xylose isomerase gene is not limited to the gene identified by SEQ ID NO: 5 and SEQ ID NO: 6. For example, it may be a gene hybridizing under stringent conditions to the full-length sequence or a partial sequence of a complementary strand of DNA comprising the nucleotide sequence as shown in SEQ ID NO: 6 and encoding a protein having xylose isomerase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM. In some embodiments, the sodium concentration may be 25 to 300 mM. The temperature is 42° C. to 68° C. In some embodiments, the temperature may be 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 5 or a gene encoding an amino acid sequence that differs from the sequence as shown in SEQ ID NO: 6 would function as a xylose isomerase gene may be determined by, for example, preparing an expression vector comprising the gene of interest incorporated into an adequate site between a promoter and a terminator, transforming an *E. coli* host using such expression vector, and assaying the xylose isomerase activity of the protein expressed. The term "xylose isomerase activity" refers to activity of isomerizing xylose into xylulose. Accordingly, xylose isomerase activity can be evaluated by preparing a solution containing xylose as a substrate, allowing the target protein to react at an adequate temperature, and measuring the amount of xylose that has decreased and/or the amount of xylulose that has been generated.

In some embodiments, a gene encoding mutant xylose isomerase comprising an amino acid sequence derived from the amino acid sequence as shown in SEQ ID NO: 6 by introduction of a particular mutation into a particular amino acid residue and having improved xylose isomerase activity may be used as a xylose isomerase gene. A specific example of a gene encoding mutant xylose isomerase is a gene encoding an amino acid sequence derived from the amino acid sequence as shown in SEQ ID NO: 6 by substitution of asparagine with cysteine at position 337. Xylose isomerase comprising an amino acid sequence derived from the amino acid sequence as shown in SEQ ID NO: 6 by substitution of asparagine with cysteine at position 337 has xylose isomerase activity superior to that of wild-type xylose isomerase. In addition, mutant xylose isomerase is not limited to the xylose isomerase resulting from substitution of asparagine with cysteine at position 337. Such mutant xylose isomerase may be prepared by substitution of, for example, asparagine at position 337 with an amino acid residue other than cysteine, asparagine at position 337 and another amino acid residue with other amino acids, or an amino acid residue other than cysteine at position 337 with another amino acid.

Meanwhile, examples of xylose metabolism-associated genes other than the xylose isomerase gene include a xylose reductase gene encoding xylose reductase that converts xylose into xylitol, a xylitol dehydrogenase gene encoding xylitol dehydrogenase that converts xylitol into xylulose, and a xylulokinase gene encoding xylulokinase that phosphorylates xylulose to produce xylulose 5-phosphate. Xylulose 5-phosphate produced by a xylulokinase enters the pentose phosphate pathway, and it is then metabolized therein.

Examples of xylose metabolism-associated genes include, but are not particularly limited to, a xylose reductase gene and a xylitol dehydrogenase gene derived from *Pichia stipitis* and a xylulokinase gene derived from *Saccharomyces cerevisiae* (see Eliasson A. et al., Appl. Environ. Microbiol., 66: 3381-3386; and Toivari M. N. et al., Metab. Eng., 3: 236-249). In addition, xylose reductase gene derived from *Candida tropicalis* or *Candida prapsilosis*, xylitol dehydrogenase gene derived from *Candida tropicalis* or *Candida prapsilosis*, and a xylulokinase gene derived from *Pichia stipitis* can be used.

Examples of yeasts that inherently have xylose-metabolizing ability include, but are not particularly limited to, *Pichia stipitis, Candida tropicalis*, and *Candida prapsilosis*.

[Arabinose Metabolism-Associated Gene]

The transgenic yeast of the present disclosure may have ability to assimilate, for example, arabinose among various pentose sugars (i.e., arabinose assimilating ability). Specifically, the transgenic yeast of the present disclosure may be capable of assimilating arabinose contained in a medium to produce ethanol. The arabinose assimilating ability can be imparted to a yeast that does not have the arabinose assimilating ability by introduction of the arabinose metabolism-associated gene, such as the L-arabinose isomerase gene, the L-ribulokinase gene, or the L-ribulose-5-phosphate-4-epimerase gene derived from prokaryotes or the L-arabitol-4-dehydrogenase gene or the L-xylose reductase gene derived from eukaryotes, into such yeast.

An example of the L-arabinose isomerase gene is the araA gene derived from *Lactobacillus plantarum*. The nucleotide sequence of the coding region of the araA gene derived from *Lactobacillus plantarum* and the amino acid sequence of the protein encoded by such gene are shown in SEQ ID NO: 7 and SEQ ID NO: 8, respectively.

The L-arabinose isomerase gene is not limited to the gene identified by SEQ ID NO: 7 and SEQ ID NO: 8, and it may be a paralogous gene or a homologous gene in the narrow sense having different nucleotide and amino acid sequences.

The L-arabinose isomerase gene is not limited to the gene identified by SEQ ID NO: 7 and SEQ ID NO: 8. For example, it may be a gene encoding a protein comprising an amino acid sequence having 70% or higher sequence similarity to or identity with the amino acid sequence as shown in SEQ ID NO: 8 and having L-arabinose isomerase activity. In some embodiments, such sequence similarity or identity may be 80% or higher, 90% or higher, or 95% or higher. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

The L-arabinose isomerase gene is not limited to the gene identified by SEQ ID NO: 7 and SEQ ID NO: 8. For example, it may be a gene encoding a protein comprising an amino acid sequence derived from the amino acid sequence as shown in SEQ ID NO: 8 by substitution, deletion, insertion, or addition of one or several amino acids and having L-arabinose isomerase activity. The term "several" used herein refers to, for example, 2 to 30. In some embodiments, it may refer to 2 to 20, 2 to 10, or 2 to 5.

The L-arabinose isomerase gene is not limited to the gene identified by SEQ ID NO: 7 and SEQ ID NO: 8. For example, it may be a gene hybridizing under stringent conditions to the full-length sequence or a partial sequence of a complementary strand of DNA comprising the nucleotide sequence as shown in SEQ ID NO: 7 and encoding a protein having L-arabinose isomerase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 mM. In some embodiments, the sodium concentration may be 25 to 300 mM. The temperature is 42° C. to 68° C. In some embodiments, the temperature may be 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 7 or a gene encoding an amino acid sequence that differs from the sequence as shown in SEQ ID NO: 8 would function as a L-arabinose isomerase gene may be determined by, for example, preparing an expression vector comprising the gene of interest incorporated into an adequate site between a promoter and a terminator, transforming an *E. coli* host using such expression vector, and assaying the L-arabinose isomerase activity of the protein expressed. The term "L-arabinose isomerase activity" refers to activity of isomerizing L-arabinose into L-ribulose. Accordingly, L-arabinose isomerase activity can be evaluated by preparing a solution containing L-arabinose as a substrate, allowing the target protein to react at an adequate temperature, and measuring the amount of L-arabinose that has decreased and/or the amount of L-ribulose that has been generated.

An example of the L-ribulokinase gene is the araB gene derived from *Lactobacillus plantarum*. The nucleotide sequence of the coding region of the araB gene derived from *Lactobacillus plantarum* and the amino acid sequence of a protein encoded by such gene are shown in SEQ ID NO: 9 and SEQ ID NO: 10, respectively.

The L-ribulokinase gene is not limited to the gene identified by SEQ ID NO: 9 and SEQ ID NO: 10. It may be a paralogous gene or a homologous gene in the narrow sense having different nucleotide and amino acid sequences.

Further, the L-ribulokinase gene is not limited to the gene identified by SEQ ID NO: 9 and SEQ ID NO: 10. For example, it may be a gene encoding a protein comprising an amino acid sequence having 70% or higher sequence similarity to or identity with the amino acid sequence as shown in SEQ ID NO: 10 and having L-ribulokinase activity. In some embodiments, such sequence similarity or identity may be 80% or higher, 90% or higher, or 95% or higher. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the L-ribulokinase gene is not limited to the gene identified by SEQ ID NO: 9 and SEQ ID NO: 10. For example, it may be a gene encoding a protein comprising an amino acid sequence derived from the amino acid sequence as shown in SEQ ID NO: 10 by substitution, deletion, insertion, or addition of one or several amino acids and having L-ribulokinase activity. The term "several" used herein refers to, for example, 2 to 30. In some embodiments, it may refer to 2 to 20, 2 to 10, or 2 to 5.

Furthermore, the L-ribulokinase gene is not limited to the gene identified by SEQ ID NO: 9 and SEQ ID NO: 10. For example, it may be a gene hybridizing under stringent conditions to the full-length sequence or a partial sequence of a complementary strand of DNA comprising the nucleotide sequence as shown in SEQ ID NO: 9 and encoding a protein having L-ribulokinase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 MM. In some embodiments, the sodium concentration may be 25 to 300 mM. The temperature is 42° C. to 68° C. In some embodiments, the temperature may be 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 9 or a gene encoding an amino acid sequence that differs from the sequence as shown in SEQ ID NO: 10 would function as an L-ribulokinase gene may be determined by, for example, preparing an expression vector comprising the gene of interest incorporated into an adequate site between a promoter and a terminator, transforming an *E. coli* host using such expression vector, and assaying the L-ribulokinase activity of the protein expressed. The term "L-ribulokinase" refers to activity of catalyzing a reaction comprising phosphorylating L-ribulose to generate L-ribulose-5-phosphate. Accordingly, L-ribulokinase activity can be evaluated by preparing a solution containing L-ribulose as a substrate, allowing the target protein to react at an adequate temperature, and measuring the amount of L-ribulose that has decreased and/or the amount of L-ribulose-5-phosphate that has been generated.

An example of the L-ribulose-5-phosphate 4-epimerase gene is the araD gene derived from *Lactobacillus plantarum*. The nucleotide sequence of the coding region of the araD gene derived from *Lactobacillus plantarum* and the amino acid sequence of the protein encoded by such gene are shown in SEQ ID NO: 11 and SEQ ID NO: 12, respectively.

The L-ribulose-5-phosphate 4-epimerase gene is not limited to the gene identified by SEQ ID NO: 11 and SEQ ID NO: 12. It may be a paralogous gene or a homologous gene in the narrow sense having different nucleotide and amino acid sequences.

The L-ribulose-5-phosphate 4-epimerase gene is not limited to the gene identified by SEQ ID NO: 11 and SEQ ID NO: 12. For example, it may be a gene encoding a protein comprising an amino acid sequence having 70% or higher sequence similarity to or identity with the amino acid sequence as shown in SEQ ID NO: 12 and having L-ribulose-5-phosphate 4-epimerase activity. In some embodiments, such sequence similarity or identity may be 80% or higher, 90% or higher, or 95% or higher. The degree of sequence similarity or identity can be determined using the BLASTN or BLASTX Program equipped with the BLAST algorithm (at default settings). The degree of sequence similarity is determined by subjecting a pair of amino acid sequences to pairwise alignment analysis, identifying completely identical amino acid residues and amino acid residues exhibiting physicochemically similar functions, determining the total number of such amino acid residues, and calculating the percentage of all the amino acid residues subjected to comparison accounted for by the total number of such amino acid residues. The degree of sequence identity is determined by subjecting a pair of amino acid sequences to pairwise alignment analysis, identifying completely identical amino acid residues, and calculating the percentage of all the amino acid residues subjected to comparison accounted for by such amino acid residues.

Further, the L-ribulose-5-phosphate 4-epimerase gene is not limited to the gene identified by SEQ ID NO: 11 and SEQ ID NO: 12. For example, it may be a gene comprising an amino acid sequence derived from the amino acid sequence as shown in SEQ ID NO: 12 by substitution, deletion, insertion, or addition of one or several amino acids and encoding a protein having L-ribulose-5-phosphate 4-epimerase activity. The term "several" used herein refers to, for example, 2 to 30. In some embodiments, it may refer to 2 to 20, 2 to 10, or 2 to 5.

Furthermore, the L-ribulose-5-phosphate 4-epimerase gene is not limited to the gene identified by SEQ ID NO: 11 and SEQ ID NO: 12. For example, it may be a gene hybridizing under stringent conditions to the full-length sequence or a partial sequence of a complementary strand of DNA comprising the nucleotide sequence as shown in SEQ ID NO: 11 and encoding a protein having L-ribulose-5-phosphate 4-epimerase activity. Under "stringent conditions," so-called specific hybrids are formed, but non-specific hybrids are not formed. For example, such conditions can be adequately determined with reference to Molecular Cloning: A Laboratory Manual (Third Edition). Specifically, the degree of stringency can be determined in accordance with the temperature and the salt concentration of a solution used for Southern hybridization and the temperature and the salt concentration of a solution used for the step of washing in Southern hybridization. Under stringent conditions, more specifically, the sodium concentration is 25 to 500 m. In some embodiments, the sodium concentration may be 25 to 300 mM. The temperature is 42° C. to 68° C. In some embodiments, the temperature may be 42° C. to 65° C. Further specifically, the sodium concentration is 5×SSC (83 mM NaCl, 83 mM sodium citrate), and the temperature is 42° C.

As described above, whether or not a gene comprising a nucleotide sequence that differs from the sequence as shown in SEQ ID NO: 11 or a gene encoding an amino acid sequence that differs from the sequence as shown in SEQ ID NO: 12 would function as a L-ribulose-5-phosphate 4-epimerase gene may be determined by, for example, preparing an expression vector comprising the gene of interest incorporated into an adequate site between a promoter and a terminator, transforming an E. coli host using such expression vector, and assaying the L-ribulose-5-phosphate 4-epimerase activity of the protein expressed. The term "L-ribulose-5-phosphate 4-epimerase activity" refers to activity of catalyzing epimerization of L-ribulose-5-phosphate and D-xylulose-5-phosphate. Accordingly, L-ribulose-5-phosphate 4-epimerase activity can be evaluated by preparing a solution containing L-ribulose-5-phosphate as a substrate, allowing the target protein to react at an adequate temperature, and measuring the amount of L-ribulose-5-phosphate that has decreased and/or the amount of D-xylulose-5-phosphate that has been generated.

[Other Genes]

The transgenic yeast of the present disclosure may further comprise another gene (or other genes) introduced thereinto, and such another gene (or other genes) is (or are) not particularly limited. For example, the transgenic yeast may comprise a gene involving the saccharide metabolism of glucose introduced thereinto. For example, a transgenic yeast can have β-glucosidase activity resulting from introduction of the β-glucosidase gene.

The term "β-glucosidase activity" used herein refers to the activity of catalyzing a hydrolysis reaction of a β-glycosidic bond of a saccharide. Specifically, β-glucosidase is capable of degrading a cellooligosaccharide, such as cellobiose, into glucose. The β-glucosidase gene can be introduced in the form of a cell-surface display gene. The term "cell-surface display gene" used herein refers to a gene that is modified to display a protein to be encoded by the gene on a cell surface. For example, a cell-surface display β-glucosidase gene results from fusion of a β-glucosidase gene with a cell-surface localized protein gene. A cell-surface localized protein is fixed and present on a yeast cell surface layer. Examples include agglutinative proteins, such as α- or a-agglutinin and FLO proteins. In general, a cell-surface localized protein comprises an N-terminal secretory signal sequence and a C-terminal GPI anchor attachment recognition signal sequence. While a cell-surface localized protein shares properties with a secretory protein in terms of the presence of a secretory signal, its secretory signal differs in that the cell-surface localized protein is transported while fixed to a cell membrane through a GPI anchor. When a cell-surface localized protein passes through a cell membrane, a GPI anchor attachment recognition signal sequence is selectively cut, it binds to a GPI anchor at a newly protruded C-terminal region, and it is then fixed to the cell membrane. Thereafter, the root of the GPI anchor is cut by phosphatidylinositol-dependent phospholipase C (PI-PLC). Subsequently, a protein separated from the cell membrane is integrated into a cell wall, fixed onto a cell surface layer, and then localized on a cell surface layer (see, for example, JP 2006-174767 A).

The β-glucosidase gene is not particularly limited, and an example is a β-glucosidase gene derived from *Aspergillus aculeatus* (Murai et al., Appl. Environ. Microbiol., 64: 4857-4861). In addition, a β-glucosidase gene derived from *Aspergillus oryzae*, a β-glucosidase gene derived from *Clostridium cellulovorans*, or a 3-glucosidase gene derived from *Saccharomycopsis fibligera* may be used.

In addition to or other than the β-glucosidase gene, a gene encoding another cellulase-constituting enzyme may have been introduced into the transgenic yeast of the present disclosure. Examples of cellulase-constituting enzymes other than β-glucosidase include exo-cellobiohydrolases that liberate cellobiose from the terminus of crystalline cellulose (CBH1 and CBH2) and endo-glucanase (EG) that cannot degrade crystalline cellulose but cleaves a non-crystalline cellulose (amorphous cellulose) chain at random.

In particular, an example of another gene to be introduced into a transgenic yeast is a gene capable of promoting the use of xylose in a medium. A specific example thereof is a gene encoding xylulokinase having activity of generating xylulose-5-phosphate using xylulose as a substrate. The metabolic flux of the pentose phosphate pathway can be improved through the introduction of the xylulokinase gene.

Further, a gene encoding an enzyme selected from the group of enzymes constituting a non-oxidative process in the pentose phosphate pathway can be introduced into the transgenic yeast of the present disclosure. Examples of enzymes constituting a non-oxidative process in the pentose phosphate pathway include ribose-5-phosphate isomerase, ribulose-5-phosphate-3-epimerase, transketolase, and transaldolase. In some embodiments, one or more genes encoding such enzymes may be introduced, two or more such genes may be introduced in combination, three or more genes may be introduced in combination, or all of the genes above may be introduced.

More specifically, the xylulokinase (XK) gene of any origin can be used without particular limitation. A wide variety of microorganisms, such as bacterial and yeasts, which assimilate xylulose, possess the XK gene. Information concerning XK genes can be obtained by searching the website of NCBI or other institutions, according to need. In some embodiments, such XK genes may be derived from yeasts, lactic acid bacteria, E. coli bacteria, or plants. An example of an XK gene is XKS1, which is an XK gene derived from the *S. cerevisiae* S288C strain (GenBank: 272979) (the nucleotide sequence and the amino acid sequence in the CDS coding region).

More specifically, a transaldolase (TAL) gene, a transketolase (TKL) gene, a ribulose-5-phosphate epimerase (RPE) gene, and a ribose-5-phosphate ketoisomerase (RKI) gene of any origin can be used without particular limitation. A wide variety of organisms comprising the pentose phosphate pathway possess such genes. For example, a common yeast such as *S. cerevisiae* possesses such genes. Information concerning such genes can be obtained from the website of NCBI or other institutions, according to need. Genes belonging to the same genus as the host eukaryotic cells, such as eukaryotic or yeast cells, may be used, and genes originating from the same species as the host eukaryotic cells may be used. A TAL1 gene, a TKL1 gene and a TKL2 gene, an RPE1 gene, and an RKI1 gene may be used as the TAL gene, the TKL genes, the RPE gene, and the RKI gene, respectively. Examples of such genes include a TAL1 gene derived from the *S. cerevisiae* 5288 strain (GenBank: U19102), a TKL1 gene derived from the *S. cerevisiae* S288 strain (GenBank: X73224), an RPE1 gene derived from the *S. cerevisiae* 5288 strain (GenBank: X83571), and an RKI1 gene derived from the *S. cerevisiae* 5288 strain (GenBank: Z75003).

<Production of Transgenic Yeast>

The transgenic yeast of the present disclosure can be produced by, for example, introducing the gene encoding glycerin dehydrogenase having a mitochondrial transport signal into a yeast having ability of metabolizing pentose, such as xylose or arabinose. Alternatively, the transgenic yeast of the present disclosure can be produced by introducing the xylose metabolism-associated enzyme gene or the arabinose metabolism-associated gene into a yeast having no pentose assimilating ability. It should be noted that another gene described above may be introduced when producing the transgenic yeast of the present disclosure.

When the glycerin dehydrogenase gene, the xylose metabolism-associated gene, the arabinose metabolism-associated gene, and other genes are to be introduced into a yeast, such genes may be simultaneously introduced thereinto, or such genes may be successively introduced with the use of different expression vectors.

Examples of host yeasts that can be used include, but are not particularly limited to, *Candida Shehatae*, *Pichia stipitis*, *Pachysolen tannophilus*, *Saccharomyces cerevisiae*, and *Schizosaccaromyces pombe*. In some embodiments, *Saccharomyces cerevisiae* may be used. Experimental yeasts may also be used from the viewpoint of experimental convenience, or industrial (practical) strains may also be used from the viewpoint of practical usefulness. Examples of industrial strains include yeasts used for the production of wine, sake, and shochu.

A host yeast may have homothallic properties. According to the technique disclosed in JP 2009-34036 A, multiple copies of genes can be easily introduced into a genome with the use of a yeast having homothallic properties. The term "yeast having homothallic properties" has the same meaning as the term "homothallic yeast." Yeasts having homothallic properties are not particularly limited, and any yeasts can be used. An example of a yeast having homothallic properties is, but is not limited to, the *Saccharomyces cerevisiae* OC-2 train (NBRC2260). Examples of other yeasts having homothallic properties include an alcohol-producing yeast (Taiken No. 396, NBRCO216) (reference: "*Alcohol kobo no shottokuser*" ("Various properties of alcohol-producing yeast"), Shuken Kaiho, No. 37, pp. 18-22, 1998.8), an ethanol-producing yeast isolated in Brazil and in Japan (reference: "*Brazil to Okinawa de bunri shita Saccharomyces cerevisiae yaseikabu no idengakuteki seishitsu*" ("Genetic properties of wild-type *Saccharomyces cerevisiae* isolated in Brazil and in Okinawa"), the Journal of the Japan Society for Bioscience, Biotechnology, and Agrochemistry, Vol. 65, No. 4, pp. 759-762, 1991.4), and 180 (reference: "*Alcohol Hakkoryoku no tsuyoi kobo no screening*" ("Screening of yeast having potent alcohol-fermenting ability"), the Journal of the Brewing Society of Japan, Vol. 82, No. 6, pp. 439-443, 1987.6). In addition, the HO gene may be introduced into a yeast exhibiting heterothallic phenotypes in an expressible manner, and the resulting strain can be used as a yeast having homothallic properties. That is, the term "yeast having homothallic properties" used herein also refers to a yeast into which the HO gene has been introduced in an expressible manner.

Promoters of genes to be introduced are not particularly limited. For example, promoters of the glyceraldehyde-3-phosphate dehydrogenase gene (TDH3), the 3-phosphoglycerate kinase gene (PGK1), and the high-osmotic pressure response 7 gene (HOR7) can be used. In some embodiments, the promoter of the pyruvate decarboxylase gene (PDC1) may be used because of its high capacity for expressing target genes in a downstream region at high levels.

Specifically, such gene may be introduced into the yeast genome together with an expression-regulated promoter or another expression-regulated region. Such gene may be introduced into a host yeast genome in such a manner that expression thereof is regulated by a promoter or another expression-regulated region of a gene that is inherently present therein.

The gene can be introduced into the genome by any conventional technique known as a yeast transformation technique. Specific examples include, but are not limited to, electroporation (Meth. Enzym., 194, p. 182, 1990), the spheroplast technique (Proc. Natl. Acad. Sci., U.S.A., 75, p. 1929, 1978), and the lithium acetate method (J. Bacteriology, 153, p. 163, 1983; Proc. Natl. Acad. Sci., U.S.A., 75, p. 1929, 1978; Methods in yeast genetics, 2000 Edition: A Cold Spring Harbor Laboratory Course Manual).

<Production of Ethanol>

When producing ethanol with the use of the transgenic yeast described above, ethanol fermentation is carried out by culture in a medium containing at least pentose, such as xylose or arabinose. Specifically, a medium in which ethanol fermentation is carried out contains, as a carbon source, at least metabolizable pentose. The medium may be supplemented with another carbon source, such as glucose, in advance.

Pentose, such as xylose or arabinose, that is contained in a medium to be used for ethanol fermentation can be derived from a biomass. In other words, a medium to be used for ethanol fermentation may comprise a cellulosic biomass and hemicellulase that generates pentose, such as xylose or arabinose, through saccharification of hemicellulose contained in a cellulosic biomass. The cellulosic biomass may have been subjected to a conventional pretreatment technique. Examples of pretreatment techniques include, but are not limited to, degradation of a lignin with a microorganism and grinding of a cellulosic biomass. For example, a ground cellulosic biomass may be subjected to pretreatment, such as soaking thereof in a dilute sulfuric acid solution, alkaline solution, or ionic solution, hydrothermal treatment, or fine grinding. Thus, the efficiency of biomass saccharification can be improved.

When producing ethanol with the use of the transgenic yeast described above, the medium may further comprise cellulose and cellulase. In such a case, the medium contains glucose generated by the action of cellulase imposed upon cellulose. When a medium used for ethanol fermentation contains cellulose, such cellulose can be derived from a biomass. In other words, a medium used for ethanol fermentation may comprise cellulase that is capable of saccharifying cellulose contained in a cellulosic biomass.

A saccharified solution resulting from saccharification of a cellulosic biomass may be added to the medium used for ethanol fermentation. In such a case, the saccharified solution contains remaining cellulose or cellulase and pentose, such as xylose or arabinose, derived from hemicellulose contained in a cellulosic biomass.

As described above, the method for producing ethanol of the present disclosure comprises a step of ethanol fermentation involving the use of at least pentose, such as xylose or arabinose, as a saccharide source. According to the method for producing ethanol of the present disclosure, ethanol can be produced through ethanol fermentation using pentose, such as xylose or arabinose, as a saccharide source. According to the method for producing ethanol with the use of the transgenic yeast of the present disclosure, ethanol fermentation is followed by recovery of ethanol from the medium. Ethanol may be recovered by any conventional means without particular limitation. After the completion of the process of ethanol fermentation mentioned above, for example, a liquid layer containing ethanol is separated from a solid layer containing the transgenic yeast or solid matter by solid-solution separation. Thereafter, ethanol contained in a liquid layer is separated and purified by distillation, so that highly purified ethanol can be recovered. The degree of ethanol purification can be adequately determined in accordance with the purpose of the use of ethanol.

In general, glycerin is known as a representative by-product of ethanol production by fermentation using a yeast. In order to improve an ethanol yield in ethanol production by fermentation, it is critical to reduce the amount of glycerin produced. When genes associated with the glycerin production pathway from glyceraldehyde-3-phosphate (i.e., GPD1, GPD2, GPP1, and GPP2 genes) are disrupted or expression levels thereof are lowered to reduce the amount of glycerin produced, however, drawbacks, such as a lowered ethanol production speed, have been pointed out (Appl. Environ. Microbiol., 2011, 77, 5857-5867; Appl. Environ. Microbiol., 2013, 79, 3273-3281).

As described in the examples below, the transgenic yeast of the present disclosure is characterized by a very low glycerin production level. It is generally known that glycerin is biosynthesized and accumulated in the cytoplasm. In order to accelerate glycerin metabolism and suppress the amount thereof produced, accordingly, it may be considered to enhance the glycerin dehydrogenase activity in the cytoplasm. While the transgenic yeast of the present disclosure comprises the glycerin dehydrogenase gene having a mitochondrial transport signal introduced thereinto to enhance the glycerin dehydrogenase activity in the mitochondria, such activity is not enhanced in the cytoplasm.

In the transgenic yeast of the present disclosure, in other words, metabolism of glycerin biosynthesized in the cytoplasm is accelerated in spite of high glycerin dehydrogenase activity levels in the mitochondria, and the amount of glycerin produced would be lowered to a significant extent. Compared with the transgenic yeast comprising the cytoplasm-localized glycerin dehydrogenase gene introduced thereinto, the amount of glycerin produced by the transgenic yeast of the present disclosure would be lowered to a greater extent.

The method for producing ethanol of the present disclosure may employ the so-called simultaneous saccharification and fermentation process in which the step of saccharification of cellulose contained in a medium with a cellulase proceeds simultaneously with the step of ethanol fermentation involving the use of saccharide sources (i.e., pentose, such as xylose or arabinose, and glucose generated by saccharification). The simultaneous saccharification and fermentation process refers to a processcarrying out saccharification of a cellulosic biomass and ethanol fermentation without distinction of step.

Methods of saccharification are not particularly limited. For example, an enzymatic method involving the use of a cellulase preparation, such as cellulase or hemicellulase, may be employed. A cellulase preparation contains a plurality of enzymes involved in degradation of a cellulose chain and a hemicellulose chain, and it exhibits a plurality of types of activity, such as endoglucanase activity, endoxylanase activity, cellobiohydrolase activity, glucosidase activity, and xylosidase activity. Cellulase preparations are not particularly limited, and examples include cellulases produced by *Trichoderma reesei* and *Acremonium cellulolyticus*. Commercially available cellulase preparations may also be used.

In the simultaneous saccharification and fermentation process, a cellulase preparation and the transgenic yeast are added to a medium containing a cellulosic biomass (a biomass after pretreatment may be used), and the transgenic yeast is cultured at given temperature. Culture may be carried out at any temperature without particular limitation, and the temperature may be 25° C. to 45° C. from the viewpoint of ethanol fermentation efficiency. In some embodiment, the temperature may be 30° C. to 40° C. The pH level of the culture solution may be 4 to 6. Agitation or shake culture may be employed. Alternatively, the simultaneous saccharification and fermentation process may be carried out irregularly in such a manner that saccharification is first carried out at an optimal temperature for an enzyme (40° C. to 70° C.), temperature is lowered to a given level (30° C. to 40° C.), and the transgenic yeast is then added thereto.

EXAMPLES

Hereafter, the present disclosure is described in greater detail with reference to the examples, although the technical scope of the present disclosure is not limited to these examples.

Example 1

In this example, effects of glycerin reduction attained by introducing the glycerin dehydrogenase gene having a mitochondrial transport signal into a transgenic yeast capable of metabolizing pentose such as xylose were inspected.

1. Method 1.1. Test Strains

Strains subjected to the fermentation test concerning the effects of glycerin reduction are as follows: a strain resulting from introduction of the NAD-dependent glycerin dehydrogenase gene (the gld1 gene) derived from a fission yeast, *Schizosaccharomyces pombe*, into a parent strain capable of metabolizing xylose and arabinose; a strain resulting from introduction of a gene derived from the gld1 gene by removal of a mitochondrial transport signal; a strain resulting from introduction of the glycerin dehydrogenase gene (gldA gene) derived from *Escherichia coli* (*E. coli*); and a strain resulting from introduction of the mitochondria-localized gldA gene comprising the gldA gene and a region encoding a sequence corresponding to the mitochondrial transport signal of the gld1 gene fused thereto. The parent strain described above was prepared by introducing a xylose metabolizing gene, the xylose isomerase (XI) gene derived from the intestinal protozoa of *Reticulitermes speratus*, and the arabinose metabolizing genes derived from lactic bacteria, *Lactobacillus plantarum*, such as the arabinose isomerase (araA) gene, the ribulokinase (araB) gene, and the ribulose 5 phosphate epimerase (araD) gene into the wine yeast, *S. cerevisiae* OC-2, reinforcing the pentose phosphate pathway genes (TKL1, TAL1, RPE1, and RKI1), the xylulokinase gene (XKS1), and the xylose and arabinose transporter gene (GAL2), and disrupting the GRE3 gene converting xylose into a by-product, xylitol.

Table 1 shows genotypes of strains used in the example.

TABLE 1

| Strain | Genotype |
| --- | --- |
| Uz2937 | GAD1/GAD1::GAL2 araA araB araD GRE3/gre3:: XI TKL1 TAL1 RPE1 RKI1 XKS1 |
| Uz3102 | PFK1/PFK1::gld1 (wild-type, mitochondria-localized) |
| | GAD1/GAD1::GAL2 araA araB araD GRE3/gre3:: XI TKL1 TAL1 RPE1 RKI1 XKS1 |
| Uz3084 | PFK1/PFK1::gld1 (mitochondrial transport signal sequence being removed) |
| | GAD1/GAD1::GAL2 araA araB araD GRE3/gre3:: XI TKL1 TAL1 RPE1 RKI1 XKS1 |
| Uz3040 | PFK1/PFK1::gldA (wild-type, cytoplasm-localized) |
| | GAD1/GAD1::GAL2 araA araB araD GRE3/gre3:: XI TKL1 TAL1 RPE1 RKI1 XKS1 |
| Uz3083 | PFK1/PFK1::gldA (mitochondrial transport signal sequence being fused, mitochondria-localized) |
| | GAD1/GAD1::GAL2 araA araB araD GRE3/gre3:: XI TKL1 TAL1 RPE1 RKI1 XKS1 |

1.2. Plasmid for XI, TKL1, TAL1, RPE1, RKI1, and XKS1 Gene Expression and GRE3 Gene Disruption A plasmid comprising a sequence necessary for introducing a mutant XI gene derived from the intestinal protozoa of *Reticulitermes speratus*, which is prepared by the total synthesis on the basis of the sequence designed by substituting asparagine with cysteine at amino acid 337 and changing codons over the entire region in accordance with the frequency of codon usage of the yeast (Katahira, S. et al., Biotechnology for Biofuels 10, 2017: 203) and TKL1, TAL1, RPE1, RKI1, and XXS1 genes derived from *S. cerevisiae* into the GRE3 gene locus of a yeast while disrupting the GRE3 gene; that is, pUC-5U_GRE3-P_HOR7-TKL1-TAL1-P_FBA1-P_ADH1-RPE1-RKI1-TEF1_P-P_TDH1-XIN337C-T_DIT1-P_TDH3-XKS1-LoxP-G418-LoxP-3U_GRE3, was prepared. The nucleotide sequence of the wild-type XI gene derived from the intestinal protozoa of *Reticulitermes speratus* and the amino acid sequence of the protein encoded by the gene are shown in SEQ ID NO: 5 and SEQ ID NO: 6, respectively.

This plasmid was constructed to comprise: the ADH1 gene comprising an HOR7 promoter added thereto; the TAL1 gene comprising an FBA1 promoter added thereto; the TAL1 gene comprising an ADH1 promoter added thereto; the RKI1 gene comprising a TEF1 promoter added thereto; the XKS1 gene comprising a TDH3 promoter and an HISS terminator added thereto; the mutant XI gene comprising a TDH1 promoter and a DIT1 terminator added thereto; a gene sequence of an upstream region of approximately 700 bp from the 5' terminus of the GRE3 gene (5U_GRE3) and a DNA sequence of a downstream region of approximately 1000 bp from the 3' terminus of the GRE3 gene (3U_GRE3) as the homologous recombination regions on the yeast genome; and the gene sequence comprising a G418 resistant gene as a marker (G418 marker). The marker gene is flanked by two LoxP sequences, and the marker gene can be removed upon Cre gene expression.

Each DNA sequence can be amplified by PCR using the primers listed in Table 2. In order to ligate DNA fragments, each primer comprises a DNA sequence added thereto in a manner such that the DNA sequence would overlap its adjacent DNA sequence by approximately 15 bp. The primers were used to amplify desired DNA fragments using, as a template, the *S. cerevisiae* OC-2 genome or DNA of the XI-synthesizing gene, and the DNA fragments were sequentially ligated using an In-Fusion HD Cloning Kit, followed by cloning into the pUC19 plasmid. Thus, the plasmid as a final product was obtained.

1.3. Plasmid for GAL2, araA, araB, and araD Gene Expression

A plasmid comprising a sequence necessary for introducing the araA gene, the araB gene, and the araD gene derived from *L. plantarum* (see WO 2008/041840) and the GAL2 gene derived from *S. cerevisiae* into the GAD1 gene locus of a yeast; that is, pUC-5U500_GAD1-P_SED1-GAL2-T_RPL15A-P_TDH3-LParaB-T_DIT_1-P_HOR7-LParaA-T_RPL41B-T_RPL3-LParaD-P_FBA1-LoxP71-T_CYC1-Crei-P_GAL1-T_LEU2-Bla-P_TEF1-LoxP66-5U_GAD1, was prepared. The nucleotide sequence of the araA gene and the amino acid sequence of the protein encoded by the gene are shown in SEQ ID NO: 7 and SEQ ID NO: 8, respectively, the nucleotide sequence of the araB gene and the amino acid sequence of the protein encoded by the gene are shown in SEQ ID NO: 9 and SEQ ID NO: 10, respectively, and the nucleotide sequence of the araD gene and the amino acid sequence of the protein encoded by the gene are shown in SEQ ID NO: 11 and SEQ ID NO: 12, respectively. The araA gene, the araB gene, and the araD gene used in this example were prepared by the total synthesis on the basis of the nucleotide sequence designed by changing codons in accordance with the frequency of codon usage of the yeast.

This plasmid was constructed to comprise: the araB gene comprising a TDH3 promoter and a DIT1 terminator added thereto; the araA gene comprising a HOR7 promoter and a RPL41B terminator added thereto; the araD gene comprising a FBA1 promoter and a RPL3 terminator added thereto; the GAL2 gene comprising a SED1 promoter and a RPL15A terminator added thereto; a gene sequence of an upstream region of approximately 500 to 1250 bp from the 5' terminus of the GAD1 gene (5U500_GAD1) and a DNA sequence of a downstream region of approximately 500 bp from a site approximately 500 bp upstream from the 5' terminus of the GAD1 gene (3U_GAD1) as the homologous recombination regions on the yeast genome; the gene sequence comprising a blasticidin resistant gene as a marker (bla marker); and a DNA recombinase Cre gene that undergoes loxP-sequence-specific recombination. The Cre gene (NCBI Accession Number: 27774771; prepared by the total synthesis by changing codons over the entire region in accordance with the frequency of codon usage of the yeast) used herein comprises a GUI promoter added thereto, it can be induced to express in a galactose-containing medium, and it comprises an intron sequence included in the COX5B gene of *S.* cerevisiae BY4742 fused thereto so as to suppress expression thereof in *E. coli* (Cre-inducible expression cassette).

The marker gene and the Cre gene are flanked by two LoxP sequences, and the marker gene and the Cre gene can be simultaneously removed upon Cre gene expression.

Each DNA sequence can be amplified by PCR using the primers shown in Table 2. In order to ligate DNA fragments, each primer comprises a DNA sequence added thereto in a manner such that the DNA sequence would overlap its adjacent DNA sequence by approximately 15 bp. With the use thereof, DNA fragments of interest were amplified using, as templates, the *S. cerevisiae* BY4742 and OC-2 genomes or DNA of the araA, araB, or araD-synthesizing gene and the pYES6/CT plasmid (bla marker, Thermo Fisher Scientific), and the DNA fragments were sequentially ligated using an In-Fusion HD Cloning Kit, followed by cloning into the pUC19 plasmid. Thus, the plasmid as a final product was obtained.

1.4. Plasmid for gld1 Gene Expression

While retaining the PFK1 gene in the PFK1 gene locus, a plasmid comprising a sequence necessary for introducing the gld1 gene derived from *S. pombe* (the gene comprising a mitochondrial transport signal) into a yeast; that is, pUC-3U_PFK1-P_TDH3-gld1-T_RPL41B-LoxP66-P_TEF 1-SAT-T_LEU2-P_GAL1-Crei-T_CYC1-LoxP71-3U300_PFK1, was prepared. The nucleotide sequence of the gld1 gene derived from *S. pombe* and the amino acid sequence of the protein encoded by the gene are shown in SEQ ID NO: 1 and SEQ ID NO: 2, respectively.

This plasmid was constructed to comprise: the gld1 gene comprising a TDH3 promoter and an RPL41B terminator added thereto; a DNA sequence of an upstream region of approximately 4000 bp from a site approximately 300 bp downstream from the 3' terminus of the PFK1 gene (3U_PFK1) and a DNA sequence of a downstream region of approximately 500 bp from a site approximately 300 bp downstream from the 3' terminus of the PFK1 gene (3U300_PFK1) as the homologous recombination regions on the yeast genome; the gene sequence comprising a nourseothricin resistant gene as a marker (nat marker); and the Cre-inducible expression cassette. The marker gene and the Cre gene are flanked by two LoxP sequences, and the marker gene and the Cre gene can be simultaneously removed upon Cre gene expression.

Each DNA sequence can be amplified by PCR using the primers shown in Table 2. In order to ligate DNA fragments, each primer comprises a DNA sequence added thereto in a manner such that the DNA sequence would overlap its adjacent DNA sequence by approximately 15 bp. With the use thereof, DNA fragments of interest were amplified using, as templates, genomic DNA of *S. cerevisiae* OC-2, genomic DNA of *E. coli* K-12, genomic DNA of *S. pombe*, and pUC-_-5_U500GAD1-P_SED1-GAL2-T_RPL15A-P_TDH3-LParaB_-T_DIT1-P_HOR7-LParaA-T_RPL41B-T_RPL3-LParaD-P_FBA1-LoxP71-T_CYC1-Crei-P_GAL1-T_LEU2-Bla-P_TEF1-LoxP66-5U_GAD1, and the DNA fragments were sequentially ligated using an In-Fusion HD Cloning Kit, followed by cloning into the pUC19 plasmid. Thus, the plasmid as a final product was obtained.

1.5. Plasmid for Cytoplasm-Localized gld1 Gene Expression

While retaining the PFK1 gene in the PFK1 gene locus, a plasmid comprising a sequence necessary for introducing the gld1 gene from which the mitochondrial transport signal has been removed into a yeast; that is, pUC-3U_PFK1-P_TDH3-gld1cy-T_RPL41B-LoxP66-P_TEF1-SAT-T_LEU2-P_GAL1-Crei-T_CYC1-LoxP71-3U300_PFK1, was prepared.

This plasmid was constructed to comprise: the cytoplasm-localized gld1 gene comprising a TDH3 promoter and an RPL41B terminator added thereto (from which a DNA sequence corresponding to 30 amino acids from the 5' terminus, which is equivalent to the mitochondrial transport signal, has been removed); 3U_PFK1 and 3U300_PKF1 as homologous recombination regions on a yeast genome; the nat marker; and a Cre-inducible expression cassette. The marker gene and the Cre gene are flanked by two LoxP sequences, and the marker gene and the Cre gene can be simultaneously removed upon Cre gene expression.

Each DNA sequence can be amplified by PCR using the primers shown in Table 2. In order to ligate DNA fragments, each primer comprises a DNA sequence added thereto in a manner such that the DNA sequence would overlap its adjacent DNA sequence by approximately 15 bp. With the use thereof, DNA fragments of interest were amplified using, as a template, pUC-3U_PFK1-P_TDH3-gld1-T_RPL41B-LoxP66-P_TEF1-SAT-T_LEU2-P_GAL1-Crei-T_CYC1-LoxP71-3U300_PFK, and the DNA fragments were sequentially ligated using an In-Fusion HD Cloning Kit, followed by cloning into the pUC19 plasmid. Thus, the plasmid as a final product was obtained.

1.6. Plasmid for gldA Gene Expression

While retaining the PFK1 gene in the PFK1 gene locus, a plasmid comprising a sequence necessary for introducing the gldA gene derived from *E. coli* into a yeast; that is, UC-3U_PFK1-P_TDH3-gldA-T_RPL41B-LoxP66-P_TEF1-SAT-T_LEU2-P_GAL1-Crei-T_CYC1-LoxP71-3U300 PFK1, was prepared. The nucleotide sequence of the gldA gene derived from *E. coli* and the amino acid sequence of the protein encoded by the gene are shown in SEQ ID NO: 3 and SEQ ID NO: 4, respectively.

This plasmid was constructed to comprise: the gldA gene comprising a TDH3 promoter and an RPL41B terminator added thereto; a DNA sequence of an upstream region of approximately 4000 bp from a site approximately 300 bp downstream from the 3' terminus of the PFK1 gene (3U_PFK1) and a DNA sequence of a downstream region of approximately 500 bp from a site approximately 300 by downstream from the 3' terminus of the PFK1 gene (3U300_PFK1) as the homologous recombination regions on the yeast genome; the gene sequence comprising a nourseothricin resistant gene as a marker (nat marker); and the Cre-inducible expression cassette. The marker gene and the Cre gene are flanked by two LoxP sequences, and the marker gene and the Cre gene can be simultaneously removed upon Cre gene expression.

Each DNA sequence can be amplified by PCR using the primers shown in Table 2. In order to ligate DNA fragments, each primer comprises a DNA sequence added thereto in a manner such that the DNA sequence would overlap its adjacent DNA sequence by approximately 15 bp. With the use thereof, DNA fragments of interest were amplified using, as templates, the gldA synthesizing gene and pUC-3U_PFK1-P_TDH3-gld1-T_RPL41B-LoxP66-P_TEF1-SAT-T_LEU2-P_GAL1-Crei-T_CYC1-LoxP71-3U300_PFK, and the DNA fragments were sequentially ligated using an In-Fusion HD Cloning Kit, followed by cloning into the pUC19 plasmid. Thus, the plasmid as a final product was obtained.

1.7. Plasmid for Mitochondria-Localized gldA Gene Expression

While retaining the PFK1 gene in the PFK1 gene locus, a plasmid comprising a sequence necessary for introducing a fusion gene comprising the gldA gene derived from E. coli and a region encoding the mitochondrial transport signal (a sequence of 30 amino acid residues from the N terminus of the amino acid sequence as shown in SEQ ID NO: 2) fused thereto into a yeast; that is, pUC-3U_PFK1-P_TDH3-gl-dAmt-T_RPL41B-LoxP66-P_TEF1-SAT-T_CYC1-LoxP71-3U300_PFK1, was prepared.

This plasmid was constructed to comprise: the gldA gene comprising a TDH3 promoter, an RPL41B terminator, and a mitochondrial transport signal of the gld1 gene derived from S. pombe added thereto; a DNA sequence of an upstream region of approximately 4000 bp from a site approximately 300 bp downstream from the 3' terminus of the PFK1 gene (3U_PFK1) and a DNA sequence of a downstream region of approximately 500 bp from a site approximately 300 bp downstream from the 3' terminus of the PFK1 gene (3U300_PFK1) as the homologous recombination regions on the yeast genome; the gene sequence comprising a nourseothricin resistant gene as a marker (nat marker); and the Cre-inducible expression cassette. The marker gene and the Cre gene are flanked by two LoxP sequences, and the marker gene and the Cre gene can be simultaneously removed upon Cre gene expression.

Each DNA sequence can be amplified by PCR using the primers shown in Table 2. In order to ligate DNA fragments, each primer comprises a DNA sequence added thereto in a manner such that the DNA sequence would overlap its adjacent DNA sequence by approximately 15 bp. With the use thereof, DNA fragments of interest were amplified using, as templates, genomic DNA of S. pombe and pUC-3U_PFK1-P_TDH3-gldA-T_RPL41B-LoxP66-P_TEF1-SAT-T_LEU2-P_GAL1-Crei-T_CYC1-LoxP71-3U300_PFK1, and the DNA fragments were sequentially ligated using an In-Fusion HD Cloning Kit, followed by cloning into the pUC19 plasmid. Thus, the plasmid as a final product was obtained.

TABLE 2

| Amplified DNA fragment | Primer sequence (5'-3') | SEQ ID No: |
|---|---|---|
| pUC-5U_GRE3-P_HOR7-TKL1-TAL1-P_FBA1-P_ADH1-RPE1-RKI1-TEF1_P-P_TDH1-XIN337C-T_DIT1-P_TDH3-XKS1-LoxP-G418-LoxP-3U_GRE3 | | |
| 5U_GRE3 | TGGGAATATTACCGCTCGAAG | 13 |
| | CTTTAAAAAATTTCCAATTTTCCTTTACG | 14 |
| HOR7 promoter | GGAAATTTTTTAAAGTCGCAGCCACGGGTCAAC | 15 |
| | GTGAATTGAGTCATTTTTTATTATTAGTCTTTTTTTTTTTTGACAATATC | 16 |
| TKL1 (tenninator region included) | ATGACTCAATTCACTGACATTGATAAGCTAG | 17 |
| | CCTTAAATCAACGTCATATTCTTTATTGGCTTTATAC | 18 |
| TA 1 (terminator region included) | GACGTTGATTTAAGGTGGTTCCGG | 19 |
| | ATGTCTGAACCAGCTCAAAAGAAAC | 20 |
| FBA1 promoter | AGCTGGTTCAGACATTTTGAATATGTATTACTTGGTTATGGTTATATATGAC | 21 |
| | CACCCAAATGAATTGAAAGCGACTGGTAGAGAGCGACTTTG | 22 |
| ADH1 promoter | GCTTTCAATTCATTTGGGTGTG | 23 |
| | TGTATATGAGATAGTTGATTGTATGCTTGG | 24 |
| RPE1 (terminator region included) | ACTATCTCATATACAATGGTCAAACCAATTATAGCTCCC | 25 |
| | AAATGGATATTGATCTAGATGGCGG | 26 |
| RKI1 (terminator region included) | GATCAATATCCATTTCTTGGTGTGTCATCGGTAGTAACGCC | 27 |
| | AGTTTTAATTACAAAATGGCTGCCGGTGTCCCAAA | 28 |
| TEF1 promoter | TTGTAATTAAAACTTAGATTAGATTGCTATGCTTTC | 29 |
| | AGGAACAGCCGTCAAGGG | 30 |
| TDH1 promoter | TTGACGGCTGTTCCTCTTCCCTTTTACAGTGCTTC | 31 |
| | AAAAATTTGAGACATTTTGTTTTGTGTGTAAATTTAGTGAAG | 32 |
| XI | ATGTCTCAAATTTTTAAGGATATCCCAG | 33 |
| | AGCGCTCTTACTTTAGCGATCGCACTAGTTTATTGAAACAAAATTTGGTT | 34 |
| DIT1 terminator | TAAAGTAAGAGCGCTACATTGGTCTACC | 35 |
| | TAACATTCAACGCTATTACTCCGCAACGCTTTTCTG | 36 |
| TDH3 promoter | TAGCGTTGAATGTTAGCGTCAACAAC | 37 |
| | TACTGAACACAACATTTTGTTTGTTTATGTGTGTTTATTCG | 38 |

TABLE 2-continued

| Amplified DNA fragment | Primer sequence (5'-3') | SEQ ID No: |
|---|---|---|
| XKS1 (terminator region included) | ATGTTGTGTTCAGTAATTCAGAGACAG | 39 |
| | AAATAATCGGTGTCATTAGATGAGAGTCTTTTCCAGTTC | 40 |
| HIS3 terminator (a part of LoxP sequence included) | TGACACCGATTATTTAAAGCTGCAG | 41 |
| | ATAATGTATGCTATACGAAGTTATAGGGAAAGATATGAGCTATACAGCGGAATTAGAGCGCGCCTCGTTC | 42 |
| CYC1 promoter (a part of LoxP sequence included) | TATAGCATACATTATACGAAGTTATACGACATCGTCGAATATG | 43 |
| | TTGAATATGGCTCATTATTAATTTAGTGTGTGTATTTGTGTTTGTGTG | 44 |
| G418 resistant gene | ATGAGCCATATTCAACGGGAAAC | 45 |
| | TTTAGTAGACATGCATTACAACCAATTAACCAATTCTG | 46 |
| URA3 terminator (a part of LoxP sequence included) | TGCATGTCTACTAAACTCACAAATTAGAGCTTCAATT | 47 |
| | ATAATGTATGCTATACGAAGTTATGGGTAATAACTGATATAATTAAATTGAAGC | 48 |
| 3U_GRE3 (a part of LoxP sequence included) | TATAGCATACATTATACGAAGTTATTGACACCGATTATTTAAAGCTGCAGCATACTCCAGCCAGTAAATCCATACTCAAC | 49 |
| | GTCTTTTTGCCAGCCAGTCC | 50 |
| pUC19 | GGCTGGCAAAAGACGGCCCTGCATTAATGAATCG | 51 |
| | GCGGTAATATTCCCAACTAGTGGATCATCCCCACG | 52 | pUC-5U500_GAD1-P_SED1-GAL2-T_RPL15A-P_TDH3-LParaB-T_DIT1-P_HOR7-LParaA-T_RPL41B-T_RPL3-LParaD-P_FBA1-LoxP71-T_CYC1-Crei-P_GAL1-T_LEU2-Bla-P_TEF1-LoxP66-5U_GAD1

| | | |
|---|---|---|
| 5U500_GAD1 | ACGGCCAGTGAATTCGGCTGATGTAATGGTATTGTTATTCAACC | 53 |
| | GCAGATGCATGGATCGTTTTTACCAGCATCAGCGCCTAGGAAC | 54 |
| SED1 promoter | AACGATCCATGCATCTGCC | 55 |
| | CTTAATAGAGCGAACGTATTTTATTTTGCTTGTCTTTGTAGTTACG | 56 |
| GAL2 | TACGTTCGCTCTATTAAGATGGCAGTTGAGGAGAACAATATG | 57 |
| | TATTTTCCATCAACCAGCTTATTCTAGCATGGCCTTGTACC | 58 |
| RPL15A terminator | GCTGGTTGATGGAAAATATAATTTTATTGG | 59 |
| | GGAAAAACGGGAAGAAAAGGAAAG | 60 |
| TDH3 promoter | TTTTCTTCCCGTTTTTCCTAGCGTTGAATGTTAGCGTC | 61 |
| | CATTTGTTTGTTTATGTGTGTTTATTCG | 62 |
| araB | ACATAAACAAACAAAATGAATTTGGTCGAAACCGC | 63 |
| | AGCGCTCTTACTTTATTAGTATTTAATAGCTTGACCAGCGGC | 64 |
| DIT1 terminator | TAAAGTAAGAGCGCTACATTGGTCTACC | 65 |
| | TTACTCCGCAACGCTTTTCTGAAC | 66 |
| HOR7 promoter | AGCGTTGCGGAGTAATCGCAGCCACGGGTCAAC | 67 |
| | TTTTTATTATTAGTCTTTTTTTTTTTGACAATATCTGTATGATTTG | 68 |
| araA | AGACTAATAATAAAAATGTTGTCCGTTCCAGATTATGAATTTTG | 69 |
| | TTGCTCTCAATCCGCTTATTTTAAGAAAGCCTTTGTCATACCAAC | 70 |
| RPL41B terminator | GCGGATTGAGAGCAAATCGTTAAGT | 71 |
| | AGAGGCATAGCGGCAAACTAAG | 72 |

TABLE 2-continued

| Amplified DNA fragment | Primer sequence (5'-3') | SEQ ID No: |
|---|---|---|
| RPL3 terminator | TGCCGCTATGCCTCTAAACAAGCTCCCAAGGGC | 73 |
| | GAAGTTTTGTTAGAAAATAAATCATTTTTTAATTG AGCATTC | 74 |
| araD | ATTTTCTAACAAAACTTCTTACTTTCTAACAGCGT GATCTTTTG | 75 |
| | AAGTAATACATATTCAAAATGTTGGAAGCATTGA AGCAAGAAG | 76 |
| FBA1 promoter (a part of LoxP sequence included) | CATTTTGAATATGTATTACTTGGTTATGGTTATAT ATGACAAAA | 77 |
| | ATAGCATACATTATACGAACGGTATGACACCGAT TATTTAAAGCTGCAGCATACACTGGTAGAGAGCG ACTTTGTATGC | 78 |
| CYC1 terminator (a part of LoxP sequence included) | TATAATGTATGCTATACGAAGTTATAGCTTGCAA ATTAAAGCCTTCGAGCGTCCCAAAACCTTC | 79 |
| | TTAGTTATGTCACGCTTACATTCACG | 80 |
| Cre 3"-terminal side | GCTTTCGAAAGAACTGATTTCGATC | 81 |
| | GCGTGACATAACTAATCAATCACCATCTTCCAAC AATC | 82 |
| COX5B-derived intron | GCTAAGCAGGCTTTGGCATGTATAACAAACACTG ATTTTTGTTTTGAGTTTTAAAAGATATCCATTT | 83 |
| | AGTTCTTTCGAAAGCCTGCAAAACTTGTGCTTGTA CACCTCGAATGTTAGTAAATGGATATCTTTT | 84 |
| Cre 5'-terminal side | CAAGGAGAAAAAACCATGTCTAACTTGTTGACTG TTC | 85 |
| | CAAAGCCTGCTTAGCTCTTTCAC | 86 |
| GAL1 promoter | TGCATGTCTACTAAACTCACAAATTAGAGCTTCA ATTTAATTATATCAGTTATTACCCACGGATTAGAA GCCGCCG | 87 |
| | GGTTTTTTCTCCTTGACGTTAAAGTATAG | 88 |
| bla marker (a part of LoxP sequence included) | TTTAGTAGACATGCATTAGCCCTCCCACACATAAC | 89 |
| | ATAGCATACATTATACGAAGTTATCCCACACACC ATAGCTTCAAAATG | 90 |
| 5U_GAD1 (a part of LoxP sequence included) | ATAGCATACATTATACGAAGTTATCCCACACACC ATAGCTTCAAAATG | 91 |
| | TCCCCGGGTACCGAGTATTCCTTGTTTTGTTCAGC CTGG | 92 | pUC-3U_PFK1-P_TDH3-gld1-T_RPL41B-LoxP66-P_TEF1-SAT-T_LEU2-P_GAL1-Crei-T_CYC1-LoxP71-3U300_PFK1

| 3U_PFK1 | ATTTAGCATCGTGCATGGG | 93 |
|---|---|---|
| | TAACATTCAACGCTAATTCCATAGCTTAGTTTAAT CAAGGC | 94 |
| TDH3 promoter | TAGCGTTGAATGTTAGCGTCAACAAC | 95 |
| | CATTTTGTTTGTTATGTGTGTTATTCG | 96 |
| gld1 | ACATAAACAAACAAAATGATTGGTCCTCGTCTTT G | 97 |
| | TTGCTCTCAATCCGCCTATGGATGAATGTCGGTCA AG | 98 |
| RPL41B terminator (a part of LoxP sequence included) | GCGGATTGAGAGCAAATCGTTAAGT | 99 |
| | ATAATGTATGCTATACGAACGGTAAGGGAAAGAT ATGAGCTATACAGCGGAATTAGAGGCATAGCGGC AAACTAAG | 100 |
| TEF1 promoter (a part of LoxP sequence included) | ATAGCATACATTATACGAAGTTATCCCACACACC ATAGCTTCAAAATG | 101 |
| | CACCGAAATCTTCATCCCTTAGATTAGATTGCTAT GC | 102 |
| nourseothricin resistant gene | ATGAAGATTTCGGTGAT | 103 |
| | TTAGGCGTCATCCTGTGCTC | 104 |

TABLE 2-continued

| Amplified DNA fragment | Primer sequence (5'-3') | SEQ ID No: |
|---|---|---|
| LEU2 terminator | CAGGATGACGCCTAAAAAGATTCTCTTTTTTATGATATTTGTAC | 105 |
| | AGGAATCATAGTTTCATGATTTTCTGTTAC | 106 |
| Cre inducible expression cassette (a part of LoxP sequence included) | GAAACTATGATTCCTACGGATTAGAAGCCGCCG | 107 |
| | TATAATGTATGCTATACGAAGTTATAGCTTGCAAATTAAAGCCTTCGAGCGTCCCAAAACCTTC | 108 |
| 3U300_PFK1 (a part of LoxP sequence included) | ATAGCATACATTATACGAACGGTATGACACCGATTATTTAAAGCTGCAGCATACTTGCATTATTCAAGTTTTAGGGTG | 109 |
| | CATTCTGTATGCGATGCCC | 110 |
| pUC19 | ATCGCATACAGAATGGATCCCCGGGTACCGAGC | 111 |
| | TGCACGATGCTAAATGATCCTCTAGAGTCGACCTGC | 112 |
| pUC-3U_PFK1-P_TDH3-gld1cy-T_RPL41B-LoxP66-P_TEF1-SAT-T_LEU2-P_GAL1-Crei-T_CYC1-LoxP71-3U300_PFK1 | | |
| Sequence other than gld1 | GCGGATTGAGAGCAAATCGTTAAGT | 113 |
| | TTTGTTTGTTTATGTGTGTTTATTCGAAACTAAGTTCTTGGTGTTTTAAAACTAA | 114 |
| gld1 with the mitochondrial transport signal being removed | CACACATAAACAAACAAAATGGCCGTTGCACAACGTTGGGGC | 115 |
| | TTGCTCTCAATCCGCCTATGGATGAATGTCGGTCAAG | 116 |
| pUC-3U_PFK1-P_TDH3-gldA-T_RPL41B-LoxP66-P_TEF1-SAT-T_LEU2-P_GAL1-Crei-T_CYC1-LoxP71-3U300_PFK1 | | |
| Sequence other than gldA | GCGGATTGAGAGCAAATCGTTAAGT | 117 |
| | TTTGTTTGTTTATGTGTGTTTATTCGAAACTAAGTTCTTGGTGTTTTAAAACTAA | 118 |
| gldA | CACACATAAACAAACAAAATGGACCGCATTATTCAATCACCGG | 119 |
| | TTGCTCTCAATCCGCTTATTCCCACTCTTGCAGGAAAC | 120 |
| pUC-3U_PFK1-P_TDH3-gldAmt-T_RPL41B-LoxP66-P_TEF1-SAT-T_LEU2-P_GAL1-Crei-T_CYC1-LoxP71-3U300_PFK1 | | |
| Sequence other than gld1 mitochondrial transport signal fused to gldA | GCGGATTGAGAGCAAATCGTTAAGT | 121 |
| | TTTGTTTGTTTATGTGTGTTTATTCGAAACTAAGTTCTTGGTGTTTTAAAACTAA | 122 |
| gld1 mitochondrial transport signal | ACATAAACAAACAAAATGATTGGTCCTCGTCTTTG | 123 |
| | TTGAATAATGCGGTCCATAGAGGCGAGCGCAAATACTTTAG | 124 |

1.8. Preparation of a Strain in which XI, TKL1, TAL1, RPE1, RKI1, and XKS1, GAL2, araA, araB, and araD Genes are Expressed and GRE3 Gene is Heterozygously Disrupted The yeast was transformed using the diploid yeast, S. cerevisiae OC-2 (NBRC2260), as a host strain and the Frozen-EZ Yeast Transformation II (ZYMO RESEARCH) in accordance with the protocols included thereinto.

A fragment obtained by amplification of the homologous recombination site of the plasmid, pUC-5U_GRE3-P_HOR7-TKL1-TAL1-P_FBA1-P_ADH1-RPE1-RKI1-TEF1_P-P_TDH1-XIN337C-T_DIT1-P_TDH3-XKS1-LoxP-G418-LoxP-3U_GRE3, by PCR was used to transform the OC2 strain, the resultant was applied to a G418-containing YPD agar medium, and the grown colonies were then purified. In addition, a fragment obtained by amplification of the homologous recombination site of the plasmid, pUC-5U500_GAD1-P_SED1-GAL2-T_RPL15A-P_TDH3-LParaB-T_DIT1-P_HOR7-LParaA-T_RPL41B-T_RPL3-LParaD-P_FBA1-LoxP71-T_CYC1-Crei-P_GAL1-T_LEU2-Bla-P_TEF1-LoxP66-5U_GAD1, by PCR was used to transform the strain mentioned above, the resultant was applied to a blasticidin-containing YPE agar medium, and the grown colonies were then purified. The resultant was designated as the Uz2937 strain. Heterozygous recombination (1 copy) of the gene introduced into the elite strain was observed, and the GRE3 gene was found to have been heterozygously disrupted.

1.9. Preparation of a Strain Into Which the Glycerin Dehydrogenase Gene has Been Introduced A fragment obtained by amplification of a region between homologous recombination sites of the plasmid prepared in 1.4. (pUC-3U_PFK1-P_TDH3-gld1-T_RPL41B-LoxP66-P_TEF1-SAT-T_LEU2-P_GAL1-Crei-T_CYC1-LoxP71-3U300_PFK1) by PCR was used to transform the Uz2937 strain. Thereafter, the resultant was applied to a nourseothricin-containing YPD agar medium, and the grown colonies were then purified. The purified strain was designated to be Uz3102.

A fragment obtained by amplification of a region between homologous recombination sites of the plasmid prepared in 1.5 (pUC-3U_PFK1-P_TDH3-gld1cy-T_RPL41B-LoxP66-P_TEF1-SAT-T_LEU2-P_GAL1-Crei-T_CYC1-LoxP71-3U300_PFK1) by PCR was used to transform the Uz2937 strain. Thereafter, the resultant was applied to a nourseothricin-containing YPD agar medium, and the grown colonies were then purified. The purified strain was designated to be Uz3084.

Also, a fragment obtained by amplification of a region between homologous recombination sites of the plasmid prepared in 1.6 (pUC-3U_PFK1-P_TDH3-gldA-T_RPL41B-LoxP66-P_TEF1-SAT-T_LEU2-P_GAL1-Crei-T_CYC1-LoxP71-3U300_PFK1) by PCR was used to transform the Uz2937 strain. Thereafter, the resultant was applied to a nourseothricin-containing YPD agar medium, and the grown colonies were then purified. The purified strain was designated to be Uz3040.

Also, a fragment obtained by amplification of a region between homologous recombination sites of the plasmid prepared in 1.7 (pUC-3U_PFK1-P_TDH3-gldAmt-T_RPL41B-LoxP66-P_TEF1-SAT-T_LEU2-P_GAL1-Crei-T_CYC1-LoxP71-3U300_PFK1) by PCR was used to transform the Uz2937 strain. Thereafter, the resultant was applied to a nourseothricin-containing YPD agar medium, and the grown colonies were then purified. The purified strain was designated to be Uz3083.

Heterozygous recombination (1 copy) was observed in all of Uz3102, Uz3084, Uz3040, and Uz3083 strains prepared above.

1.10. Fermentation Test in Flask

The test strains (Uz3102, Uz3084, Uz3040, or Uz3083) were inoculated into 100-ml baffled flasks each comprising 20 ml of YPD liquid medium (yeast extract concentration: 10 g/l; peptone concentration: 20 g/l; and glucose concentration: 20 g/l), and culture was conducted at 30° C. and 120 rpm for 24 hours. The strains were harvested and inoculated into a 24-deep-well plate comprising 4.9 ml of a medium for ethanol production per well (concentration: 0.3 g dry cells/l), and the fermentation test was carried out by agitation culture at 230 rpm with an amplitude of 25 mm at 31° C. Each well of the 24-deep-well plate was covered by a silicon cap with a check valve to allow the generated carbon dioxide gas to be discharged outside while preventing oxygen from entering into the wells. Thus, the condition in per well was maintained anaerobic.

In this example, a medium containing glucose as a saccharide source (glucose: 227 g/l, yeast extract: 10 g/l, and acetic acid 2.3 g/l) and a medium containing molasses as a saccharide source (a medium containing 260 g/l of sucrose, glucose, and fructose in total) were used as media for ethanol production.

Glycerin and ethanol in the fermentation liquor were assayed by HPLC (Prominence; Shimadzu Corporation) under the conditions described below.

Column: Aminex HPX-87H

Mobile phase: 0.01 N $H_2SO_4$

Flow rate: 0.6 ml/min

Temperature: 50° C.

Detection apparatus: Differential refractometer (RID-10A)

Sucrose, fructose, and glucose in the fermentation liquor containing molasses were assayed by HPLC (Prominence; Shimadzu Corporation) under the conditions described below.

Column: SHIMADZU Shim-pack SPR-Na

Mobile phase: 0.01 N $H_2SO_4$.

Flow rate: 0.6 ml/min

Temperature: 60° C.

Detection apparatus: Differential refractometer (RID-10A)

Table 3 shows the results of the fermentation test concerning Uz3102 into which the mitochondria-localized gld1 gene had been introduced and Uz3084 into which the cytoplasm-localized gld1 gene had been introduced, which was carried out with the use of a medium containing glucose as a saccharide source. A glycerin yield indicates a ratio of glycerin produced (g) relative to saccharide consumed (g).

TABLE 3

|  | Uz2937 control | Uz3102 gld1 mitochondria-localied | Uz3084 gld1 cytoplasm-localized |
|---|---|---|---|
| Glycerin concentration (g/l) | 4.7 | 4.1 | 4.8 |
| Glycerin yield (g/g) | 0.021 | 0.018 | 0.021 |
| Standard deviation of glycerin concentration | 0.14 | 0.04 | 0.13 |
| Ethanol concentration (g/l) | 99.9 | 104.5 | 103.9 |
| Standard deviation of ethanol | 2.9 | 0.02 | 0.28 |
| Glucose concentration (g/l) | 6.9 | 0 | 0.4 |

Table 4 shows the results of the fermentation test concerning Uz3102 and Uz3084, which was carried out with the use of a medium containing molasses as a saccharide source.

TABLE 4

|  | Uz2937 control | Uz3102 gld1 mitochondria-localied | Uz3084 gld1 cytoplasm-localized |
|---|---|---|---|
| Glycerin concentration (g/l) | 14.0 | 13.2 | 12.2 |
| Glycerin yield (g/g) | 0.074 | 0.072 | 0.074 |
| Standard deviation of glycerin concentration | 0.78 | 0.17 | 0.10 |
| Ethanol concentration (g/l) | 69.4 | 71.7 | 64.7 |
| Standard deviation of ethanol | 2.25 | 0.31 | 1.08 |
| Glucose concentration (g/l) | 70.4 | 77.1 | 95.6 |

Further, Table 5 shows the results of the fermentation test concerning Uz3083 into which the mitochondria-localized gldA gene had been introduced and Uz3040 into which the cytoplasm-localized gldA gene had been introduced, which was carried out with the use of a medium containing molasses as a saccharide source.

TABLE 5

|  | Uz2937 control | Uz3083 gldA mitochondria-localied | Uz3040 gldA cytoplasm-localized |
|---|---|---|---|
| Glycerin concentration (g/l) | 13.3 | 11.6 | 11.0 |
| Glycerin yield (g/g) | 0.68 | 0.61 | 0.58 |
| Standard deviation of glycerin concentration | 0.11 | 0.19 | 0.19 |
| Ethanol concentration (g/l) | 70.0 | 75.4 | 73.7 |
| Standard deviation of ethanol | 0.75 | 0.78 | 1.12 |
| Glucose concentration (g/l) | 4.82 | 6.43 | 7.49 |

As demonstrated in Tables 3 to 5, in comparison with the control strain (Uz2937) and the strains into which the cytoplasm-localized gene of glycerin dehydrogenase had been introduced (Uz3084 and Uz3040), the strains into which the mitochondria-localized gene of glycerin dehydrogenase had been introduced (Uz3102 and Uz3083) exhibited an equivalent glycerin yield, a higher saccharide consumption speed, and a higher amount of ethanol production in a medium selectively comprising molasses or glucose as a saccharide source.

In general, glycerin as a by-product of ethanol fermentation is biosynthesized and accumulated in the cytoplasm. Dihydroxyacetone kinase equivalent to an enzyme existing downstream of glycerin dehydrogenase in the glycerin metabolizing pathway of a yeast is a cytoplasm-localized enzyme. Thus, a strain into which a cytoplasm-localized glycerin dehydrogenase gene has been introduced is presumed to have lower glycerin concentration and higher ethanol concentration. In contrast to such presumption, introduction of the mitochondria-localized glycerin dehydrogenase gene did not show a significant difference in the glycerin metabolism, and ethanol yield would be improved to a significant extent, as demonstrated in the examples.

What is claimed is:

1. A transgenic yeast having pentose assimilating ability and comprising a heterologous nucleic acid that comprises a nucleotide sequence encoding a glycerin dehydrogenase having a mitochondrial transport signal,
   wherein said yeast is *Saccharomyces cerevisiae*,
   wherein said glycerin dehydrogenase localizes to the mitochondria of said transgenic yeast, and
   wherein the amount of glycerin produced by said transgenic yeast is lower than the amount of glycerin produced by a transgenic yeast that comprises a cytoplasm-localized glycerin dehydrogenase.

2. The transgenic yeast according to claim 1, wherein the glycerin dehydrogenase is an NAD-dependent glycerin dehydrogenase having activity of converting NAD into NADH.

3. The transgenic yeast according to claim 1, wherein the nucleotide sequence encoding the glycerin dehydrogenase encodes the protein (a) or (b):
   (a) a protein comprising the amino acid sequence as shown in SEQ ID NO: 2; or
   (b) a protein comprising an amino acid sequence having 90% or higher sequence identity to the amino acid sequence as shown in SEQ ID NO: 2, having mitochondrial locality, and having activity of generating dihydroxyacetone using glycerin as a substrate.

4. The transgenic yeast according to claim 1, wherein the nucleotide sequence encoding the glycerin dehydrogenase encodes a fusion protein comprising a mitochondrial transport signal and the protein (a) or (b):
   (a) a protein comprising the amino acid sequence as shown in SEQ ID NO: 4; or
   (b) a protein comprising an amino acid sequence having 90% or higher sequence identity to the amino acid sequence as shown in SEQ ID NO: 4, and having activity of generating dihydroxyacetone using glycerin as a substrate.

5. The transgenic yeast according to claim 1, wherein the pentose is xylose and/or arabinose.

6. The transgenic yeast according to claim 1, which comprises a xylose isomerase gene introduced thereinto and has xylose assimilating ability.

7. The transgenic yeast according to claim 6, which further comprises a xylulokinase gene introduced thereinto.

8. The transgenic yeast according to claim 1, which comprises a gene encoding an enzyme selected from a group of enzymes constituting a non-oxidative process in the pentose phosphate pathway introduced thereinto.

9. The transgenic yeast according to claim 8, wherein the group of enzymes constituting a non-oxidative process in the pentose phosphate pathway includes ribose-5-phosphate isomerase, ribulose-5-phosphate-3-epimerase, transketolase, and transaldolase.

10. A method for producing ethanol comprising a step of ethanol fermentation by culturing the transgenic yeast according to claim 1 in a medium containing assimilable pentose.

11. The method for producing ethanol according to claim 10, wherein the medium contains cellulose and the ethanol fermentation proceeds simultaneously at least with cellulose saccharification.

\* \* \* \* \*

```
                       SEQUENCE LISTING

<160> NUMBER OF SEQ ID NOS: 124

<210> SEQ ID NO 1
<211> LENGTH: 1353
<212> TYPE: DNA
<213> ORGANISM: Schizosaccharomyces pombe
<220> FEATURE:
<221> NAME/KEY: CDS
<222> LOCATION: (1)..(1353)

<400> SEQUENCE: 1 atg att ggt cct cgt ctt tgc gct gca acc cct cgc ttc cct ctc gtt       48
Met Ile Gly Pro Arg Leu Cys Ala Ala Thr Pro Arg Phe Pro Leu Val
 1               5                  10                  15 tcc ctc gcc cac agg aac tct aaa gta ttt gcg ctc gcc tct tcc aat       96
Ser Leu Ala His Arg Asn Ser Lys Val Phe Ala Leu Ala Ser Ser Asn
             20                  25                  30 gcc gtt gca caa cgt tgg ggc aaa cgc ttt tat gct cct att gaa acg      144
Ala Val Ala Gln Arg Trp Gly Lys Arg Phe Tyr Ala Pro Ile Glu Thr
         35                  40                  45 gag acg cct cac aaa gtt ggt gta gag ttt gaa gaa tcc aaa gat cgc      192
Glu Thr Pro His Lys Val Gly Val Glu Phe Glu Glu Ser Lys Asp Arg
     50                  55                  60 att ttc acc tct cct caa aag tat gtt cag ggt cgt cat gcc ttc act      240
Ile Phe Thr Ser Pro Gln Lys Tyr Val Gln Gly Arg His Ala Phe Thr
 65                  70                  75                  80 aga tcc tat atg tat gtc aaa aaa tgg gcc act aaa tca gct gtc gtg      288
Arg Ser Tyr Met Tyr Val Lys Lys Trp Ala Thr Lys Ser Ala Val Val
                 85                  90                  95 ctt gcc gac cag aac gta tgg aac att tgt gcc aat aaa att gtc gat      336
Leu Ala Asp Gln Asn Val Trp Asn Ile Cys Ala Asn Lys Ile Val Asp
            100                 105                 110 tct ctt tct caa aac gga atg act gtc acc aaa ctg gtc ttt ggc ggc      384
Ser Leu Ser Gln Asn Gly Met Thr Val Thr Lys Leu Val Phe Gly Gly
        115                 120                 125 gag gca agc ttg gtg gaa ctg gat aaa ctt cgc aaa cag tgc cct gat      432
Glu Ala Ser Leu Val Glu Leu Asp Lys Leu Arg Lys Gln Cys Pro Asp
    130                 135                 140 gat act caa gtc atc att gga gtt ggt ggt aaa acc atg gat tcc          480
Asp Thr Gln Val Ile Ile Gly Val Gly Gly Lys Thr Met Asp Ser
145                 150                 155                 160 gca aag tat att gct cat tcc atg aat ctt cca tcc atc att tgt cct      528
Ala Lys Tyr Ile Ala His Ser Met Asn Leu Pro Ser Ile Ile Cys Pro
                165                 170                 175 act act gcc tcc tct gat gcc gct act tcc tct ctt tcc gtc att tac      576
Thr Thr Ala Ser Ser Asp Ala Ala Thr Ser Ser Leu Ser Val Ile Tyr
            180                 185                 190 act cct gac ggt caa ttc caa aaa tac agc ttt tac ccc ctt aat ccc      624
Thr Pro Asp Gly Gln Phe Gln Lys Tyr Ser Phe Tyr Pro Leu Asn Pro
```

```
                195                 200                 205
aac ctc att ttc atc gat acc gat gtg att gtt cgc gct ccc gtc cgc     672
Asn Leu Ile Phe Ile Asp Thr Asp Val Ile Val Arg Ala Pro Val Arg
    210                 215                 220 ttc ctt att agt ggc att ggt gat gct ttg tcc acc tgg gtg gaa act     720
Phe Leu Ile Ser Gly Ile Gly Asp Ala Leu Ser Thr Trp Val Glu Thr
225                 230                 235                 240 gaa tcc gtt att cgc tca aat tcc act tcc ttt gcc gga ggt gtg gcc     768
Glu Ser Val Ile Arg Ser Asn Ser Thr Ser Phe Ala Gly Gly Val Ala
                245                 250                 255 tcc att gct ggc cgt tac att gcc cgt gct tgc aaa gac act ctt gaa     816
Ser Ile Ala Gly Arg Tyr Ile Ala Arg Ala Cys Lys Asp Thr Leu Glu
            260                 265                 270 aag tat gcc ctg agc gct att ctt tcc aac act cgc ggt gtt tgt acc     864
Lys Tyr Ala Leu Ser Ala Ile Leu Ser Asn Thr Arg Gly Val Cys Thr
        275                 280                 285 gag gca ttt gag aac gtg gtc gag gcc aac aca ttg atg tct ggt cta     912
Glu Ala Phe Glu Asn Val Val Glu Ala Asn Thr Leu Met Ser Gly Leu
    290                 295                 300 ggc ttt gaa aac ggt ggt ctt gct gct gct cat gcc atc cat aac ggt     960
Gly Phe Glu Asn Gly Gly Leu Ala Ala Ala His Ala Ile His Asn Gly
305                 310                 315                 320 atg acc gcc atc cac ggt ccc gtt cat cgt tta atg cat ggt gaa aag    1008
Met Thr Ala Ile His Gly Pro Val His Arg Leu Met His Gly Glu Lys
                325                 330                 335 gtt gct tac ggt acc tta gtt caa gtt gtt ttg gag gat tgg ccg ttg    1056
Val Ala Tyr Gly Thr Leu Val Gln Val Val Leu Glu Asp Trp Pro Leu
            340                 345                 350 gaa gac ttc aat aat ctt gct tct ttt atg gca aaa tgt cat ctt ccc    1104
Glu Asp Phe Asn Asn Leu Ala Ser Phe Met Ala Lys Cys His Leu Pro
        355                 360                 365 att acc ctt gag gaa ctt ggt att ccc aac gta acc gat gaa gag tta    1152
Ile Thr Leu Glu Glu Leu Gly Ile Pro Asn Val Thr Asp Glu Glu Leu
    370                 375                 380 ttg atg gta ggt aga gct act ttg cga cct gat gag agt att cac aac    1200
Leu Met Val Gly Arg Ala Thr Leu Arg Pro Asp Glu Ser Ile His Asn
385                 390                 395                 400 atg tca aag aag ttc aat cca tct caa att gct gac gct att aaa gcc    1248
Met Ser Lys Lys Phe Asn Pro Ser Gln Ile Ala Asp Ala Ile Lys Ala
                405                 410                 415 gtt gac tcc tat tca caa aaa tgg caa gaa caa act gga tgg acc gag    1296
Val Asp Ser Tyr Ser Gln Lys Trp Gln Glu Gln Thr Gly Trp Thr Glu
            420                 425                 430 cgt ttt aga tta ccc cct tct cgt cat agt cct cac ttg acc gac att    1344
Arg Phe Arg Leu Pro Pro Ser Arg His Ser Pro His Leu Thr Asp Ile
        435                 440                 445 cat cca tag                                                        1353
His Pro
    450

<210> SEQ ID NO 2
<211> LENGTH: 450
<212> TYPE: PRT
<213> ORGANISM: Schizosaccharomyces pombe

<400> SEQUENCE: 2

Met Ile Gly Pro Arg Leu Cys Ala Ala Thr Pro Arg Phe Pro Leu Val
1               5                   10                  15

Ser Leu Ala His Arg Asn Ser Lys Val Phe Ala Leu Ala Ser Ser Asn
            20                  25                  30
```

Ala Val Ala Gln Arg Trp Gly Lys Arg Phe Tyr Ala Pro Ile Glu Thr
                35                  40                  45

Glu Thr Pro His Lys Val Gly Val Glu Phe Glu Ser Lys Asp Arg
     50                  55                  60

Ile Phe Thr Ser Pro Gln Lys Tyr Val Gln Gly Arg His Ala Phe Thr
65                  70                  75                  80

Arg Ser Tyr Met Tyr Val Lys Lys Trp Ala Thr Lys Ser Ala Val Val
                85                  90                  95

Leu Ala Asp Gln Asn Val Trp Asn Ile Cys Ala Asn Lys Ile Val Asp
            100                 105                 110

Ser Leu Ser Gln Asn Gly Met Thr Val Thr Lys Leu Val Phe Gly Gly
            115                 120                 125

Glu Ala Ser Leu Val Glu Leu Asp Lys Leu Arg Lys Gln Cys Pro Asp
        130                 135                 140

Asp Thr Gln Val Ile Ile Gly Val Gly Gly Lys Thr Met Asp Ser
145                 150                 155                 160

Ala Lys Tyr Ile Ala His Ser Met Asn Leu Pro Ser Ile Ile Cys Pro
                165                 170                 175

Thr Thr Ala Ser Ser Asp Ala Ala Thr Ser Ser Leu Ser Val Ile Tyr
            180                 185                 190

Thr Pro Asp Gly Gln Phe Gln Lys Tyr Ser Phe Tyr Pro Leu Asn Pro
        195                 200                 205

Asn Leu Ile Phe Ile Asp Thr Asp Val Ile Val Arg Ala Pro Val Arg
210                 215                 220

Phe Leu Ile Ser Gly Ile Gly Asp Ala Leu Ser Thr Trp Val Glu Thr
225                 230                 235                 240

Glu Ser Val Ile Arg Ser Asn Ser Thr Ser Phe Ala Gly Gly Val Ala
                245                 250                 255

Ser Ile Ala Gly Arg Tyr Ile Ala Arg Ala Cys Lys Asp Thr Leu Glu
            260                 265                 270

Lys Tyr Ala Leu Ser Ala Ile Leu Ser Asn Thr Arg Gly Val Cys Thr
        275                 280                 285

Glu Ala Phe Glu Asn Val Val Glu Ala Asn Thr Leu Met Ser Gly Leu
    290                 295                 300

Gly Phe Glu Asn Gly Gly Leu Ala Ala Ala His Ala Ile His Asn Gly
305                 310                 315                 320

Met Thr Ala Ile His Gly Pro Val His Arg Leu Met His Gly Glu Lys
                325                 330                 335

Val Ala Tyr Gly Thr Leu Val Gln Val Val Leu Glu Asp Trp Pro Leu
            340                 345                 350

Glu Asp Phe Asn Asn Leu Ala Ser Phe Met Ala Lys Cys His Leu Pro
        355                 360                 365

Ile Thr Leu Glu Glu Leu Gly Ile Pro Asn Val Thr Asp Glu Glu Leu
    370                 375                 380

Leu Met Val Gly Arg Ala Thr Leu Arg Pro Asp Glu Ser Ile His Asn
385                 390                 395                 400

Met Ser Lys Lys Phe Asn Pro Ser Gln Ile Ala Asp Ala Ile Lys Ala
                405                 410                 415

Val Asp Ser Tyr Ser Gln Lys Trp Gln Glu Gln Thr Gly Trp Thr Glu
            420                 425                 430

Arg Phe Arg Leu Pro Pro Ser Arg His Ser Pro His Leu Thr Asp Ile
        435                 440                 445

His Pro
    450

<210> SEQ ID NO 3
<211> LENGTH: 1104
<212> TYPE: DNA
<213> ORGANISM: Escherichia coli
<220> FEATURE:
<221> NAME/KEY: CDS
<222> LOCATION: (1)..(1104)

<400> SEQUENCE: 3

| | | |
|---|---|---|
| atg gac cgc att att caa tca ccg ggt aaa tac atc cag ggc gct gat<br>Met Asp Arg Ile Ile Gln Ser Pro Gly Lys Tyr Ile Gln Gly Ala Asp<br>1               5                   10                  15 | | 48 |
| gtg att aat cgt ctg ggc gaa tac ctg aag ccg ctg gca gaa cgc tgg<br>Val Ile Asn Arg Leu Gly Glu Tyr Leu Lys Pro Leu Ala Glu Arg Trp<br>            20                  25                  30 | | 96 |
| tta gtg gtg ggt gac aaa ttt gtt tta ggt ttt gct caa tcc act gtc<br>Leu Val Val Gly Asp Lys Phe Val Leu Gly Phe Ala Gln Ser Thr Val<br>        35                  40                  45 | | 144 |
| gag aaa agc ttt aaa gat gct gga ctg gta gta gaa att gcg ccg ttt<br>Glu Lys Ser Phe Lys Asp Ala Gly Leu Val Val Glu Ile Ala Pro Phe<br>    50                  55                  60 | | 192 |
| ggc ggt gaa tgt tcg caa aat gag atc gac cgt ctg cgt ggc atc gcg<br>Gly Gly Glu Cys Ser Gln Asn Glu Ile Asp Arg Leu Arg Gly Ile Ala<br>65                  70                  75                  80 | | 240 |
| gag act gcg cag tgt ggc gca att ctc ggt atc ggt ggc gga aaa acc<br>Glu Thr Ala Gln Cys Gly Ala Ile Leu Gly Ile Gly Gly Gly Lys Thr<br>                85                  90                  95 | | 288 |
| ctc gat act gcc aaa gca ctg gca cat ttc atg ggt gtt ccg gta gcg<br>Leu Asp Thr Ala Lys Ala Leu Ala His Phe Met Gly Val Pro Val Ala<br>            100                 105                 110 | | 336 |
| atc gca ccg act atc gcc tct acc gat gca ccg tgc agc gca ttg tct<br>Ile Ala Pro Thr Ile Ala Ser Thr Asp Ala Pro Cys Ser Ala Leu Ser<br>        115                 120                 125 | | 384 |
| gtt atc tac acc gat gag ggt gag ttt gac cgc tat ctg ctg ttg cca<br>Val Ile Tyr Thr Asp Glu Gly Glu Phe Asp Arg Tyr Leu Leu Leu Pro<br>    130                 135                 140 | | 432 |
| aat aac ccg aat atg gtc att gtc gac acc aaa atc gtc gct ggc gca<br>Asn Asn Pro Asn Met Val Ile Val Asp Thr Lys Ile Val Ala Gly Ala<br>145                 150                 155                 160 | | 480 |
| cct gca cgt ctg tta gcg gcg ggt atc ggc gat gcg ctg gca acc tgg<br>Pro Ala Arg Leu Leu Ala Ala Gly Ile Gly Asp Ala Leu Ala Thr Trp<br>                165                 170                 175 | | 528 |
| ttt gaa gcg cgt gcc tgc tct cgt agc ggc gcg acc acc atg gcg ggc<br>Phe Glu Ala Arg Ala Cys Ser Arg Ser Gly Ala Thr Thr Met Ala Gly<br>            180                 185                 190 | | 576 |
| ggc aag tgc acc cag gct gcg ctg gca ctg gct gaa ctg tgc tac aac<br>Gly Lys Cys Thr Gln Ala Ala Leu Ala Leu Ala Glu Leu Cys Tyr Asn<br>        195                 200                 205 | | 624 |
| acc ctg ctg gaa gaa ggc gaa aaa gcg atg ctt gct gcc gaa cag cat<br>Thr Leu Leu Glu Glu Gly Glu Lys Ala Met Leu Ala Ala Glu Gln His<br>    210                 215                 220 | | 672 |
| gta gtg act ccg gcg ctg gag cgc gtg att gaa gcg aac acc tat ttg<br>Val Val Thr Pro Ala Leu Glu Arg Val Ile Glu Ala Asn Thr Tyr Leu<br>225                 230                 235                 240 | | 720 |
| agc ggt gtt ggt ttt gaa agt ggt ggt ctg gct gcg gcg cac gca gtg<br>Ser Gly Val Gly Phe Glu Ser Gly Gly Leu Ala Ala Ala His Ala Val<br>                245                 250                 255 | | 768 |
| cat aac ggc ctg acc gct atc ccg gac gcg cat cac tat tat cac ggt<br> | | 816 |

-continued

```
                His Asn Gly Leu Thr Ala Ile Pro Asp Ala His His Tyr Tyr His Gly
                            260                 265                 270 gaa aaa gtg gca ttc ggt acg ctg acg cag ctg gtt ctg gaa aat gcg        864
Glu Lys Val Ala Phe Gly Thr Leu Thr Gln Leu Val Leu Glu Asn Ala
            275                 280                 285 ccg gtg gag gaa atc gaa acc gta gct gcc ctt agc cat gcg gta ggt        912
Pro Val Glu Glu Ile Glu Thr Val Ala Ala Leu Ser His Ala Val Gly
290                 295                 300 ttg cca ata act ctc gct caa ctg gat att aaa gaa gat gtc ccg gcg        960
Leu Pro Ile Thr Leu Ala Gln Leu Asp Ile Lys Glu Asp Val Pro Ala
305                 310                 315                 320 aaa atg cga att gtg gca gaa gcg gca tgt gca gaa ggt gaa acc att       1008
Lys Met Arg Ile Val Ala Glu Ala Ala Cys Ala Glu Gly Glu Thr Ile
                325                 330                 335 cac aac atg cct ggc ggc gcg acg cca gat cag gtt tac gcc gct ctg       1056
His Asn Met Pro Gly Gly Ala Thr Pro Asp Gln Val Tyr Ala Ala Leu
            340                 345                 350 ctg gta gcc gac cag tac ggt cag cgt ttc ctg caa gag tgg gaa taa       1104
Leu Val Ala Asp Gln Tyr Gly Gln Arg Phe Leu Gln Glu Trp Glu
        355                 360                 365

<210> SEQ ID NO 4
<211> LENGTH: 367
<212> TYPE: PRT
<213> ORGANISM: Escherichia coli

<400> SEQUENCE: 4

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Lys Thr
            85                  90                  95

Leu Asp Thr Ala Lys Ala Leu Ala His Phe Met Gly Val Pro Val Ala
        100                 105                 110

Ile Ala Pro Thr Ile Ala Ser Thr Asp Ala Pro Cys Ser Ala Leu Ser
    115                 120                 125

Val Ile Tyr Thr Asp Glu Gly Glu Phe Asp Arg Tyr Leu Leu Leu Pro
130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
            165                 170                 175

Phe Glu Ala Arg Ala Cys Ser Arg Ser Gly Ala Thr Thr Met Ala Gly
        180                 185                 190

Gly Lys Cys Thr Gln Ala Ala Leu Ala Leu Ala Glu Leu Cys Tyr Asn
    195                 200                 205

Thr Leu Leu Glu Glu Gly Glu Lys Ala Met Leu Ala Ala Glu Gln His
210                 215                 220

Val Val Thr Pro Ala Leu Glu Arg Val Ile Glu Ala Asn Thr Tyr Leu
225                 230                 235                 240
```

```
Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
    290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 5
<211> LENGTH: 1320
<212> TYPE: DNA
<213> ORGANISM: Unknown
<220> FEATURE:
<223> OTHER INFORMATION: Obtained from Intestinal Protist of
      Reticulitermes speratus
<220> FEATURE:
<221> NAME/KEY: CDS
<222> LOCATION: (1)..(1320)

<400> SEQUENCE: 5 atg tct caa att ttt aag gat atc cca gtt att aaa tat gaa ggt cca      48
Met Ser Gln Ile Phe Lys Asp Ile Pro Val Ile Lys Tyr Glu Gly Pro
1               5                   10                  15 gct tcc aag aat cct ttg agt ttc aaa tac tac gat gca aac aag gtt      96
Ala Ser Lys Asn Pro Leu Ser Phe Lys Tyr Tyr Asp Ala Asn Lys Val
            20                  25                  30 att gat ggt aaa cca atg aag gaa cat ttg aga tac gca atg gct tgg     144
Ile Asp Gly Lys Pro Met Lys Glu His Leu Arg Tyr Ala Met Ala Trp
        35                  40                  45 tgg cat aat ttg tgt gct acc ggt caa gat atg ttt ggt cct ggt act     192
Trp His Asn Leu Cys Ala Thr Gly Gln Asp Met Phe Gly Pro Gly Thr
    50                  55                  60 gca gat aaa tcc ttc ggt agt aag aca gtt ggt acc atg gaa cat gca     240
Ala Asp Lys Ser Phe Gly Ser Lys Thr Val Gly Thr Met Glu His Ala
65                  70                  75                  80 cat gct aaa gtt gat gct ggt ttt gaa ttc atg tcc aag ttg ggt gtt     288
His Ala Lys Val Asp Ala Gly Phe Glu Phe Met Ser Lys Leu Gly Val
                85                  90                  95 gaa tac ttc tgt ttc cat gat gct gat ttg gtt cca gaa gca gat act     336
Glu Tyr Phe Cys Phe His Asp Ala Asp Leu Val Pro Glu Ala Asp Thr
            100                 105                 110 ttg agt gaa aca aac aaa aga ttg gat gaa atc gct gaa cat atc gtt     384
Leu Ser Glu Thr Asn Lys Arg Leu Asp Glu Ile Ala Glu His Ile Val
        115                 120                 125 gct aag caa aag gca act ggt att aaa tgt ttg tgg ggt aca gca aat     432
Ala Lys Gln Lys Ala Thr Gly Ile Lys Cys Leu Trp Gly Thr Ala Asn
    130                 135                 140 ttg ttt tct aac cct aga ttc tta aat ggt tct ggt tct tca aac tca     480
Leu Phe Ser Asn Pro Arg Phe Leu Asn Gly Ser Gly Ser Ser Asn Ser
145                 150                 155                 160
```

-continued

| | | |
|---|---|---|
| gct gat gtt tat gca tac gct gca gct caa att aaa aag gct ttg gat<br>Ala Asp Val Tyr Ala Tyr Ala Ala Ala Gln Ile Lys Lys Ala Leu Asp<br>165                        170                    175 | 528 |
| ttg act gtt aaa ttt ggt ggt gtt ggt tat gtt ttc tgg ggt ggt aga<br>Leu Thr Val Lys Phe Gly Gly Val Gly Tyr Val Phe Trp Gly Gly Arg<br>180                        185                    190 | 576 |
| gaa ggt tac gaa acc ttg ttg aac act gat gtt aag ttc gaa caa gaa<br>Glu Gly Tyr Glu Thr Leu Leu Asn Thr Asp Val Lys Phe Glu Gln Glu<br>195                        200                    205 | 624 |
| aac atc gct aac ttg atg cat ttg gca gtt act tac ggt aga tca atc<br>Asn Ile Ala Asn Leu Met His Leu Ala Val Thr Tyr Gly Arg Ser Ile<br>210                        215                    220 | 672 |
| ggt ttt aaa ggt gac ttc tac att gaa cca aaa cct aag gaa cca aca<br>Gly Phe Lys Gly Asp Phe Tyr Ile Glu Pro Lys Pro Lys Glu Pro Thr<br>225                        230                    235                    240 | 720 |
| aag cat caa tat gat ttt gat gca gct act aca att ggt ttc att aga<br>Lys His Gln Tyr Asp Phe Asp Ala Ala Thr Thr Ile Gly Phe Ile Arg<br>245                        250                    255 | 768 |
| caa tac ggt ttg gaa aag gat ttc aag ttg aac atc gaa gca aac cat<br>Gln Tyr Gly Leu Glu Lys Asp Phe Lys Leu Asn Ile Glu Ala Asn His<br>260                        265                    270 | 816 |
| gct aca tta gca ggt cat acc ttc caa cat gat ttg aga atc tct gct<br>Ala Thr Leu Ala Gly His Thr Phe Gln His Asp Leu Arg Ile Ser Ala<br>275                        280                    285 | 864 |
| att aat ggc atg tta ggt tca gtt gat gca aac aca ggt gac cca ttg<br>Ile Asn Gly Met Leu Gly Ser Val Asp Ala Asn Thr Gly Asp Pro Leu<br>290                        295                    300 | 912 |
| tta ggt tgg gat acc gat gaa ttt cct tat tcc gtt tac gat acc act<br>Leu Gly Trp Asp Thr Asp Glu Phe Pro Tyr Ser Val Tyr Asp Thr Thr<br>305                        310                    315                    320 | 960 |
| ttg gct atg tac gaa att att aag gca ggt ggt ttg acc ggt ggt ttg<br>Leu Ala Met Tyr Glu Ile Ile Lys Ala Gly Gly Leu Thr Gly Gly Leu<br>325                        330                    335 | 1008 |
| aat ttt gat tcc aag gtt aga aga cca agt tac aca cat gaa gat ttg<br>Asn Phe Asp Ser Lys Val Arg Arg Pro Ser Tyr Thr His Glu Asp Leu<br>340                        345                    350 | 1056 |
| ttt tac ggt ttc att ttg ggt atg gat tct ttc gct ttg ggt ttg att<br>Phe Tyr Gly Phe Ile Leu Gly Met Asp Ser Phe Ala Leu Gly Leu Ile<br>355                        360                    365 | 1104 |
| aaa gca aag gct ttg att gca gat ggt aga ttg gat tca ttc gtt aag<br>Lys Ala Lys Ala Leu Ile Ala Asp Gly Arg Leu Asp Ser Phe Val Lys<br>370                        375                    380 | 1152 |
| gat aga tac gct tct tac ggt tca ggt att ggt gct aag att aga gat<br>Asp Arg Tyr Ala Ser Tyr Gly Ser Gly Ile Gly Ala Lys Ile Arg Asp<br>385                        390                    395                    400 | 1200 |
| cat tct gca act ttg gaa gaa tta gca gct tat gca tta gct aaa gat<br>His Ser Ala Thr Leu Glu Glu Leu Ala Ala Tyr Ala Leu Ala Lys Asp<br>405                        410                    415 | 1248 |
| aca gtt gct ttg cct ggt tcc ggt aga caa gaa tac tta gaa agt att<br>Thr Val Ala Leu Pro Gly Ser Gly Arg Gln Glu Tyr Leu Glu Ser Ile<br>420                        425                    430 | 1296 |
| att aac caa att ttg ttt caa taa<br>Ile Asn Gln Ile Leu Phe Gln<br>435 | 1320 |

<210> SEQ ID NO 6
<211> LENGTH: 439
<212> TYPE: PRT
<213> ORGANISM: Unknown
<220> FEATURE:
<223> OTHER INFORMATION: Synthetic Construct

```
<400> SEQUENCE: 6

Met Ser Gln Ile Phe Lys Asp Ile Pro Val Ile Lys Tyr Glu Gly Pro
1               5                   10                  15

Ala Ser Lys Asn Pro Leu Ser Phe Lys Tyr Tyr Asp Ala Asn Lys Val
            20                  25                  30

Ile Asp Gly Lys Pro Met Lys Glu His Leu Arg Tyr Ala Met Ala Trp
        35                  40                  45

Trp His Asn Leu Cys Ala Thr Gly Gln Asp Met Phe Gly Pro Gly Thr
    50                  55                  60

Ala Asp Lys Ser Phe Gly Ser Lys Thr Val Gly Thr Met Glu His Ala
65                  70                  75                  80

His Ala Lys Val Asp Ala Gly Phe Glu Phe Met Ser Lys Leu Gly Val
                85                  90                  95

Glu Tyr Phe Cys Phe His Asp Ala Asp Leu Val Pro Glu Ala Asp Thr
            100                 105                 110

Leu Ser Glu Thr Asn Lys Arg Leu Asp Glu Ile Ala Glu His Ile Val
        115                 120                 125

Ala Lys Gln Lys Ala Thr Gly Ile Lys Cys Leu Trp Gly Thr Ala Asn
130                 135                 140

Leu Phe Ser Asn Pro Arg Phe Leu Asn Gly Ser Gly Ser Asn Ser
145                 150                 155                 160

Ala Asp Val Tyr Ala Tyr Ala Ala Gln Ile Lys Lys Ala Leu Asp
                165                 170                 175

Leu Thr Val Lys Phe Gly Gly Val Gly Tyr Val Phe Trp Gly Gly Arg
            180                 185                 190

Glu Gly Tyr Glu Thr Leu Leu Asn Thr Asp Val Lys Phe Glu Gln Glu
        195                 200                 205

Asn Ile Ala Asn Leu Met His Leu Ala Val Thr Tyr Gly Arg Ser Ile
210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Thr Ile Gly Phe Ile Arg
                245                 250                 255

Gln Tyr Gly Leu Glu Lys Asp Phe Lys Leu Asn Ile Glu Ala Asn His
            260                 265                 270

Ala Thr Leu Ala Gly His Thr Phe Gln His Asp Leu Arg Ile Ser Ala
        275                 280                 285

Ile Asn Gly Met Leu Gly Ser Val Asp Ala Asn Thr Gly Asp Pro Leu
290                 295                 300

Leu Gly Trp Asp Thr Asp Glu Phe Pro Tyr Ser Val Tyr Asp Thr Thr
305                 310                 315                 320

Leu Ala Met Tyr Glu Ile Ile Lys Ala Gly Gly Leu Thr Gly Gly Leu
                325                 330                 335

Asn Phe Asp Ser Lys Val Arg Arg Pro Ser Tyr Thr His Glu Asp Leu
            340                 345                 350

Phe Tyr Gly Phe Ile Leu Gly Met Asp Ser Phe Ala Leu Gly Leu Ile
        355                 360                 365

Lys Ala Lys Ala Leu Ile Ala Asp Gly Arg Leu Asp Ser Phe Val Lys
370                 375                 380

Asp Arg Tyr Ala Ser Tyr Gly Ser Gly Ile Gly Ala Lys Ile Arg Asp
385                 390                 395                 400

His Ser Ala Thr Leu Glu Glu Leu Ala Ala Tyr Ala Leu Ala Lys Asp
```

```
                        405                 410                 415
Thr Val Ala Leu Pro Gly Ser Gly Arg Gln Glu Tyr Leu Glu Ser Ile
            420                 425                 430

Ile Asn Gln Ile Leu Phe Gln
        435

<210> SEQ ID NO 7
<211> LENGTH: 1425
<212> TYPE: DNA
<213> ORGANISM: Lactobacillus plantarum
<220> FEATURE:
<221> NAME/KEY: CDS
<222> LOCATION: (1)..(1425)

<400> SEQUENCE: 7 atg ttg tcc gtt cca gat tat gaa ttt tgg ttc gtc act ggt tct caa      48
Met Leu Ser Val Pro Asp Tyr Glu Phe Trp Phe Val Thr Gly Ser Gln
1               5                   10                  15 cat ttg tac ggt gaa gaa caa ttg aag tca gtt gca aag gac gcc caa      96
His Leu Tyr Gly Glu Glu Gln Leu Lys Ser Val Ala Lys Asp Ala Gln
            20                  25                  30 gat atc gca gac aaa ttg aat gcc tct ggt aaa ttg cct tac aag gtt     144
Asp Ile Ala Asp Lys Leu Asn Ala Ser Gly Lys Leu Pro Tyr Lys Val
        35                  40                  45 gtc ttt aaa gat gtt atg act aca gct gaa tca ata aca aac ttc atg     192
Val Phe Lys Asp Val Met Thr Thr Ala Glu Ser Ile Thr Asn Phe Met
    50                  55                  60 aag gaa gtc aac tac aac gat aaa gta gcc ggt gtt atc aca tgg atg     240
Lys Glu Val Asn Tyr Asn Asp Lys Val Ala Gly Val Ile Thr Trp Met
65                  70                  75                  80 cat acc ttt tct cca gct aag aat tgg att aga ggt act gaa ttg ttg     288
His Thr Phe Ser Pro Ala Lys Asn Trp Ile Arg Gly Thr Glu Leu Leu
                85                  90                  95 caa aag cca ttg ttg cac ttg gct aca caa tat ttg aac aac ata cct     336
Gln Lys Pro Leu Leu His Leu Ala Thr Gln Tyr Leu Asn Asn Ile Pro
            100                 105                 110 tac gca gat atc gac ttc gat tac atg aat ttg aac caa tca gct cat     384
Tyr Ala Asp Ile Asp Phe Asp Tyr Met Asn Leu Asn Gln Ser Ala His
        115                 120                 125 ggt gac aga gaa tac gcc tac atc aac gct aga ttg caa aag cac aac     432
Gly Asp Arg Glu Tyr Ala Tyr Ile Asn Ala Arg Leu Gln Lys His Asn
    130                 135                 140 aag atc gta tat ggt tac tgg ggt gac gaa gat gtt caa gaa caa ata     480
Lys Ile Val Tyr Gly Tyr Trp Gly Asp Glu Asp Val Gln Glu Gln Ile
145                 150                 155                 160 gct aga tgg gaa gat gta gcc gtt gct tac aat gaa tct ttt aaa gtc     528
Ala Arg Trp Glu Asp Val Ala Val Ala Tyr Asn Glu Ser Phe Lys Val
                165                 170                 175 aag gta gca aga ttc ggt gac acc atg aga aac gtt gca gtc act gaa     576
Lys Val Ala Arg Phe Gly Asp Thr Met Arg Asn Val Ala Val Thr Glu
            180                 185                 190 ggt gac aag gtt gaa gcc caa att aaa atg ggt tgg act gtc gat tat     624
Gly Asp Lys Val Glu Ala Gln Ile Lys Met Gly Trp Thr Val Asp Tyr
        195                 200                 205 tac ggt atc ggt gac ttg gta gaa gaa att aat aag gtc tcc gac gca     672
Tyr Gly Ile Gly Asp Leu Val Glu Glu Ile Asn Lys Val Ser Asp Ala
    210                 215                 220 gat gta gac aaa gaa tat gcc gat ttg gaa agt aga tac gaa atg gtt     720
Asp Val Asp Lys Glu Tyr Ala Asp Leu Glu Ser Arg Tyr Glu Met Val
225                 230                 235                 240
```

| | | |
|---|---|---|
| caa ggt gac aac gac gca gat acc tat aaa cat tcc gta aga gtt caa<br>Gln Gly Asp Asn Asp Ala Asp Thr Tyr Lys His Ser Val Arg Val Gln<br>                245                              250                    255 | 768 | |
| ttg gcc caa tac tta ggt att aaa aga ttt ttg gaa aga ggt ggt tat<br>Leu Ala Gln Tyr Leu Gly Ile Lys Arg Phe Leu Glu Arg Gly Gly Tyr<br>                    260                            265                         270 | 816 | |
| aca gct ttt acc act aat ttc gaa gat ttg tgg ggt atg gaa caa ttg<br>Thr Ala Phe Thr Thr Asn Phe Glu Asp Leu Trp Gly Met Glu Gln Leu<br>                275                            280                        285 | 864 | |
| cca ggt tta gct agt caa ttg tta att aga gat ggt tac ggt ttt ggt<br>Pro Gly Leu Ala Ser Gln Leu Leu Ile Arg Asp Gly Tyr Gly Phe Gly<br>            290                            295                        300 | 912 | |
| gca gag ggt gac tgg aaa aca gct gca ttg ggt aga gtt atg aag atc<br>Ala Glu Gly Asp Trp Lys Thr Ala Ala Leu Gly Arg Val Met Lys Ile<br>305                    310                            315                        320 | 960 | |
| atg tct cat aat aag caa aca gct ttc atg gaa gat tat acc ttg gac<br>Met Ser His Asn Lys Gln Thr Ala Phe Met Glu Asp Tyr Thr Leu Asp<br>                              325                            330                        335 | 1008 | |
| tta aga cat ggt cac gaa gcc att ttg ggt tca cat atg tta gaa gtc<br>Leu Arg His Gly His Glu Ala Ile Leu Gly Ser His Met Leu Glu Val<br>                340                            345                        350 | 1056 | |
| gat cca tcc ata gca agt gac aag cca aga gtc gaa gta cac cct ttg<br>Asp Pro Ser Ile Ala Ser Asp Lys Pro Arg Val Glu Val His Pro Leu<br>            355                            360                        365 | 1104 | |
| gat att ggt ggt aaa gat gac cct gca aga tta gtt ttt acc ggt tcc<br>Asp Ile Gly Gly Lys Asp Asp Pro Ala Arg Leu Val Phe Thr Gly Ser<br>        370                            375                            380 | 1152 | |
| gaa ggt gaa gct ata gat gtt act gtc gca gat ttt aga gac ggt ttc<br>Glu Gly Glu Ala Ile Asp Val Thr Val Ala Asp Phe Arg Asp Gly Phe<br>385                    390                            395                        400 | 1200 | |
| aag atg atc agt tat gct gta gat gca aat aag cca gaa gct gaa aca<br>Lys Met Ile Ser Tyr Ala Val Asp Ala Asn Lys Pro Glu Ala Glu Thr<br>                              405                            410                        415 | 1248 | |
| cca aac ttg cct gtt gca aag caa tta tgg acc cct aaa atg ggt ttg<br>Pro Asn Leu Pro Val Ala Lys Gln Leu Trp Thr Pro Lys Met Gly Leu<br>            420                            425                        430 | 1296 | |
| aaa aag ggt gcc tta gaa tgg atg caa gct ggt ggt ggt cat cac act<br>Lys Lys Gly Ala Leu Glu Trp Met Gln Ala Gly Gly Gly His His Thr<br>                435                            440                        445 | 1344 | |
| atg ttg tct ttt tca ttg aca gaa gaa caa atg gaa gat tac gcc act<br>Met Leu Ser Phe Ser Leu Thr Glu Glu Gln Met Glu Asp Tyr Ala Thr<br>        450                            455                            460 | 1392 | |
| atg gtt ggt atg aca aag gct ttc tta aaa taa<br>Met Val Gly Met Thr Lys Ala Phe Leu Lys<br>465                    470 | 1425 | |

```
<210> SEQ ID NO 8
<211> LENGTH: 474
<212> TYPE: PRT
<213> ORGANISM: Lactobacillus plantarum

<400> SEQUENCE: 8

Met Leu Ser Val Pro Asp Tyr Glu Phe Trp Phe Val Thr Gly Ser Gln
1               5                   10                  15

His Leu Tyr Gly Glu Glu Gln Leu Lys Ser Val Ala Lys Asp Ala Gln
            20                  25                  30

Asp Ile Ala Asp Lys Leu Asn Ala Ser Gly Lys Leu Pro Tyr Lys Val
        35                  40                  45

Val Phe Lys Asp Val Met Thr Thr Ala Glu Ser Ile Thr Asn Phe Met
    50                  55                  60
```

```
Lys Glu Val Asn Tyr Asn Asp Lys Val Ala Gly Val Ile Thr Trp Met
 65                  70                  75                  80

His Thr Phe Ser Pro Ala Lys Asn Trp Ile Arg Gly Thr Glu Leu Leu
                 85                  90                  95

Gln Lys Pro Leu Leu His Leu Ala Thr Gln Tyr Leu Asn Asn Ile Pro
            100                 105                 110

Tyr Ala Asp Ile Asp Phe Asp Tyr Met Asn Leu Asn Gln Ser Ala His
        115                 120                 125

Gly Asp Arg Glu Tyr Ala Tyr Ile Asn Ala Arg Leu Gln Lys His Asn
    130                 135                 140

Lys Ile Val Tyr Gly Tyr Trp Gly Asp Glu Asp Val Gln Glu Gln Ile
145                 150                 155                 160

Ala Arg Trp Glu Asp Val Ala Val Ala Tyr Asn Glu Ser Phe Lys Val
                165                 170                 175

Lys Val Ala Arg Phe Gly Asp Thr Met Arg Asn Val Ala Val Thr Glu
            180                 185                 190

Gly Asp Lys Val Glu Ala Gln Ile Lys Met Gly Trp Thr Val Asp Tyr
        195                 200                 205

Tyr Gly Ile Gly Asp Leu Val Glu Glu Ile Asn Lys Val Ser Asp Ala
    210                 215                 220

Asp Val Asp Lys Glu Tyr Ala Asp Leu Glu Ser Arg Tyr Glu Met Val
225                 230                 235                 240

Gln Gly Asp Asn Asp Ala Asp Thr Tyr Lys His Ser Val Arg Val Gln
                245                 250                 255

Leu Ala Gln Tyr Leu Gly Ile Lys Arg Phe Leu Glu Arg Gly Gly Tyr
            260                 265                 270

Thr Ala Phe Thr Thr Asn Phe Glu Asp Leu Trp Gly Met Glu Gln Leu
        275                 280                 285

Pro Gly Leu Ala Ser Gln Leu Leu Ile Arg Asp Gly Tyr Gly Phe Gly
    290                 295                 300

Ala Glu Gly Asp Trp Lys Thr Ala Ala Leu Gly Arg Val Met Lys Ile
305                 310                 315                 320

Met Ser His Asn Lys Gln Thr Ala Phe Met Glu Asp Tyr Thr Leu Asp
                325                 330                 335

Leu Arg His Gly His Glu Ala Ile Leu Gly Ser His Met Leu Glu Val
            340                 345                 350

Asp Pro Ser Ile Ala Ser Asp Lys Pro Arg Val Glu Val His Pro Leu
        355                 360                 365

Asp Ile Gly Gly Lys Asp Pro Ala Arg Leu Val Phe Thr Gly Ser
    370                 375                 380

Glu Gly Glu Ala Ile Asp Val Thr Val Ala Asp Phe Arg Asp Gly Phe
385                 390                 395                 400

Lys Met Ile Ser Tyr Ala Val Asp Ala Asn Lys Pro Glu Ala Glu Thr
                405                 410                 415

Pro Asn Leu Pro Val Ala Lys Gln Leu Trp Thr Pro Lys Met Gly Leu
            420                 425                 430

Lys Lys Gly Ala Leu Glu Trp Met Gln Ala Gly Gly His His Thr
        435                 440                 445

Met Leu Ser Phe Ser Leu Thr Glu Glu Gln Met Glu Asp Tyr Ala Thr
    450                 455                 460

Met Val Gly Met Thr Lys Ala Phe Leu Lys
465                 470
```

```
<210> SEQ ID NO 9
<211> LENGTH: 1602
<212> TYPE: DNA
<213> ORGANISM: Lactobacillus plantarum
<220> FEATURE:
<221> NAME/KEY: CDS
<222> LOCATION: (1)..(1602)

<400> SEQUENCE: 9
```

| | | | | | | | | | | | | | | | | |
|---|---|---|---|---|---|---|---|---|---|---|---|---|---|---|---|---|
| atg | aat | ttg | gtc | gaa | acc | gca | caa | gcc | ata | aaa | act | ggt | aaa | gtt | tct | 48 |
| Met | Asn | Leu | Val | Glu | Thr | Ala | Gln | Ala | Ile | Lys | Thr | Gly | Lys | Val | Ser | |
| 1 | | | | 5 | | | | | 10 | | | | | 15 | | |
| ttg | ggt | atc | gaa | ttg | ggt | tca | act | aga | att | aaa | gct | gtt | ttg | atc | aca | 96 |
| Leu | Gly | Ile | Glu | Leu | Gly | Ser | Thr | Arg | Ile | Lys | Ala | Val | Leu | Ile | Thr | |
| | | | 20 | | | | | 25 | | | | | 30 | | | |
| gat | gac | ttc | aac | acc | att | gca | tcc | ggt | agt | tat | gtc | tgg | gaa | aac | caa | 144 |
| Asp | Asp | Phe | Asn | Thr | Ile | Ala | Ser | Gly | Ser | Tyr | Val | Trp | Glu | Asn | Gln | |
| | | 35 | | | | | 40 | | | | | 45 | | | | |
| ttc | gta | gat | ggt | aca | tgg | acc | tac | gct | ttg | gaa | gac | gtc | tgg | acc | ggt | 192 |
| Phe | Val | Asp | Gly | Thr | Trp | Thr | Tyr | Ala | Leu | Glu | Asp | Val | Trp | Thr | Gly | |
| | 50 | | | | | 55 | | | | | 60 | | | | | |
| atc | caa | caa | tcc | tat | act | caa | ttg | gct | gca | gat | gtt | aga | tct | aag | tac | 240 |
| Ile | Gln | Gln | Ser | Tyr | Thr | Gln | Leu | Ala | Ala | Asp | Val | Arg | Ser | Lys | Tyr | |
| 65 | | | | | 70 | | | | | 75 | | | | | 80 | |
| cat | atg | tca | ttg | aag | cac | atc | aac | gca | atc | ggt | atc | tct | gcc | atg | atg | 288 |
| His | Met | Ser | Leu | Lys | His | Ile | Asn | Ala | Ile | Gly | Ile | Ser | Ala | Met | Met | |
| | | | | 85 | | | | | 90 | | | | | 95 | | |
| cat | ggt | tat | ttg | gct | ttc | gat | caa | caa | gca | aag | ttg | tta | gtt | cca | ttc | 336 |
| His | Gly | Tyr | Leu | Ala | Phe | Asp | Gln | Gln | Ala | Lys | Leu | Leu | Val | Pro | Phe | |
| | | | 100 | | | | | 105 | | | | | 110 | | | |
| aga | aca | tgg | aga | aat | aac | att | acc | ggt | caa | gcc | gct | gat | gaa | ttg | aca | 384 |
| Arg | Thr | Trp | Arg | Asn | Asn | Ile | Thr | Gly | Gln | Ala | Ala | Asp | Glu | Leu | Thr | |
| | | 115 | | | | | 120 | | | | | 125 | | | | |
| gaa | ttg | ttc | gac | ttc | aac | ata | cct | caa | aga | tgg | tca | atc | gcc | cat | ttg | 432 |
| Glu | Leu | Phe | Asp | Phe | Asn | Ile | Pro | Gln | Arg | Trp | Ser | Ile | Ala | His | Leu | |
| | 130 | | | | | 135 | | | | | 140 | | | | | |
| tac | caa | gct | atc | ttg | aac | aac | gaa | gcc | cac | gta | aag | caa | gtt | gat | ttt | 480 |
| Tyr | Gln | Ala | Ile | Leu | Asn | Asn | Glu | Ala | His | Val | Lys | Gln | Val | Asp | Phe | |
| 145 | | | | | 150 | | | | | 155 | | | | | 160 | |
| atc | act | aca | ttg | gct | ggt | tac | gta | act | tgg | aaa | ttg | tcc | ggt | gaa | aag | 528 |
| Ile | Thr | Thr | Leu | Ala | Gly | Tyr | Val | Thr | Trp | Lys | Leu | Ser | Gly | Glu | Lys | |
| | | | | 165 | | | | | 170 | | | | | 175 | | |
| gtt | tta | ggt | att | ggt | gac | gct | agt | ggt | gtc | ttt | cca | ata | gat | gaa | acc | 576 |
| Val | Leu | Gly | Ile | Gly | Asp | Ala | Ser | Gly | Val | Phe | Pro | Ile | Asp | Glu | Thr | |
| | | | 180 | | | | | 185 | | | | | 190 | | | |
| act | gac | aca | tac | aac | caa | act | atg | ttg | aca | aaa | ttc | tcc | caa | ttg | gat | 624 |
| Thr | Asp | Thr | Tyr | Asn | Gln | Thr | Met | Leu | Thr | Lys | Phe | Ser | Gln | Leu | Asp | |
| | | 195 | | | | | 200 | | | | | 205 | | | | |
| aag | gtt | aag | cct | tac | agt | tgg | gac | att | aga | cac | ata | ttg | cca | aga | gtc | 672 |
| Lys | Val | Lys | Pro | Tyr | Ser | Trp | Asp | Ile | Arg | His | Ile | Leu | Pro | Arg | Val | |
| | 210 | | | | | 215 | | | | | 220 | | | | | |
| tta | cct | gct | ggt | gca | att | gcc | ggt | aaa | ttg | act | gca | gcc | ggt | gca | tcc | 720 |
| Leu | Pro | Ala | Gly | Ala | Ile | Ala | Gly | Lys | Leu | Thr | Ala | Ala | Gly | Ala | Ser | |
| 225 | | | | | 230 | | | | | 235 | | | | | 240 | |
| ttg | tta | gat | caa | agt | ggt | aca | tta | gac | gca | ggt | tca | gtt | att | gcc | cca | 768 |
| Leu | Leu | Asp | Gln | Ser | Gly | Thr | Leu | Asp | Ala | Gly | Ser | Val | Ile | Ala | Pro | |
| | | | | 245 | | | | | 250 | | | | | 255 | | |
| cct | gaa | ggt | gac | gct | ggt | act | ggt | atg | gtt | ggt | aca | aat | tct | gtc | aga | 816 |
| Pro | Glu | Gly | Asp | Ala | Gly | Thr | Gly | Met | Val | Gly | Thr | Asn | Ser | Val | Arg | |
| | | | 260 | | | | | 265 | | | | | 270 | | | |

| | | |
|---|---|---|
| aaa aga act ggt aac att tca gta ggt acc tct gct ttt tca atg aac<br>Lys Arg Thr Gly Asn Ile Ser Val Gly Thr Ser Ala Phe Ser Met Asn<br>     275                        280                   285 | 864 |
| gtt ttg gat aag cca ttg tct aag gtt tac aga gat atc gac att gtc<br>Val Leu Asp Lys Pro Leu Ser Lys Val Tyr Arg Asp Ile Asp Ile Val<br>290                       295                       300 | 912 |
| atg act cca gat ggt tca cct gtt gct atg gtt cat gtc aat aac tgt<br>Met Thr Pro Asp Gly Ser Pro Val Ala Met Val His Val Asn Asn Cys<br>305                       310                   315               320 | 960 |
| tct tca gac atc aac gct tgg gca aca att ttt cac gaa ttc gct gca<br>Ser Ser Asp Ile Asn Ala Trp Ala Thr Ile Phe His Glu Phe Ala Ala<br>                  325                   330               335 | 1008 |
| aga ttg ggt atg gaa ttg aag cca gat aga ttg tac gaa act ttg ttc<br>Arg Leu Gly Met Glu Leu Lys Pro Asp Arg Leu Tyr Glu Thr Leu Phe<br>            340                       345                   350 | 1056 |
| tta gaa tct aca aga gcc gat gct gac gca ggt ggt tta gca aat tat<br>Leu Glu Ser Thr Arg Ala Asp Ala Asp Ala Gly Gly Leu Ala Asn Tyr<br>355                       360                   365 | 1104 |
| tcc tac caa agt ggt gaa aac atc acc aaa att caa gct ggt aga cca<br>Ser Tyr Gln Ser Gly Glu Asn Ile Thr Lys Ile Gln Ala Gly Arg Pro<br>    370                       375                   380 | 1152 |
| ttg ttc gtt aga act cct aac tct aag ttt tca ttg cca aac ttc atg<br>Leu Phe Val Arg Thr Pro Asn Ser Lys Phe Ser Leu Pro Asn Phe Met<br>385                       390                   395               400 | 1200 |
| ttg act caa ttg tat gcc gct ttc gca cct ttg caa ttg ggt atg gat<br>Leu Thr Gln Leu Tyr Ala Ala Phe Ala Pro Leu Gln Leu Gly Met Asp<br>                  405                   410               415 | 1248 |
| atc ttg gtt aac gaa gaa cat gtc caa aca gac gta atg atc gct caa<br>Ile Leu Val Asn Glu Glu His Val Gln Thr Asp Val Met Ile Ala Gln<br>            420                       425                   430 | 1296 |
| ggt ggt ttg ttt aga acc cca gta att ggt caa caa gtt ttg gcc aat<br>Gly Gly Leu Phe Arg Thr Pro Val Ile Gly Gln Gln Val Leu Ala Asn<br>            435                       440                   445 | 1344 |
| gct tta aac ata cca atc acc gta atg tct act gca ggt gaa ggt ggt<br>Ala Leu Asn Ile Pro Ile Thr Val Met Ser Thr Ala Gly Glu Gly Gly<br>450                       455                       460 | 1392 |
| cct tgg ggt atg gca gtt tta gcc aat ttc gct tgc aga caa act gct<br>Pro Trp Gly Met Ala Val Leu Ala Asn Phe Ala Cys Arg Gln Thr Ala<br>465                       470                   475               480 | 1440 |
| atg aac ttg gaa gat ttc ttg gac caa gaa gtt ttc aaa gaa cca gaa<br>Met Asn Leu Glu Asp Phe Leu Asp Gln Glu Val Phe Lys Glu Pro Glu<br>                  485                   490               495 | 1488 |
| tcc atg aca ttg agt cca gaa cct gaa aga gtc gcc ggt tat aga gaa<br>Ser Met Thr Leu Ser Pro Glu Pro Glu Arg Val Ala Gly Tyr Arg Glu<br>            500                       505                   510 | 1536 |
| ttc att caa aga tac caa gct ggt tta cct gtt gaa gca gcc gct ggt<br>Phe Ile Gln Arg Tyr Gln Ala Gly Leu Pro Val Glu Ala Ala Ala Gly<br>515                       520                   525 | 1584 |
| caa gct att aaa tac taa<br>Gln Ala Ile Lys Tyr<br>    530 | 1602 |

<210> SEQ ID NO 10
<211> LENGTH: 533
<212> TYPE: PRT
<213> ORGANISM: Lactobacillus plantarum

<400> SEQUENCE: 10

Met Asn Leu Val Glu Thr Ala Gln Ala Ile Lys Thr Gly Lys Val Ser
1               5                   10                  15

```
Leu Gly Ile Glu Leu Gly Ser Thr Arg Ile Lys Ala Val Leu Ile Thr
             20                  25                  30

Asp Asp Phe Asn Thr Ile Ala Ser Gly Ser Tyr Val Trp Glu Asn Gln
             35                  40                  45

Phe Val Asp Gly Thr Trp Thr Tyr Ala Leu Glu Asp Val Trp Thr Gly
             50                  55                  60

Ile Gln Gln Ser Tyr Thr Gln Leu Ala Ala Asp Val Arg Ser Lys Tyr
 65                  70                  75                  80

His Met Ser Leu Lys His Ile Asn Ala Ile Gly Ile Ser Ala Met Met
                 85                  90                  95

His Gly Tyr Leu Ala Phe Asp Gln Gln Ala Lys Leu Leu Val Pro Phe
                100                 105                 110

Arg Thr Trp Arg Asn Asn Ile Thr Gly Gln Ala Ala Asp Glu Leu Thr
                115                 120                 125

Glu Leu Phe Asp Phe Asn Ile Pro Gln Arg Trp Ser Ile Ala His Leu
            130                 135                 140

Tyr Gln Ala Ile Leu Asn Asn Glu Ala His Val Lys Gln Val Asp Phe
145                 150                 155                 160

Ile Thr Thr Leu Ala Gly Tyr Val Thr Trp Lys Leu Ser Gly Glu Lys
                165                 170                 175

Val Leu Gly Ile Gly Asp Ala Ser Gly Val Phe Pro Ile Asp Glu Thr
                180                 185                 190

Thr Asp Thr Tyr Asn Gln Thr Met Leu Thr Lys Phe Ser Gln Leu Asp
            195                 200                 205

Lys Val Lys Pro Tyr Ser Trp Asp Ile Arg His Ile Leu Pro Arg Val
210                 215                 220

Leu Pro Ala Gly Ala Ile Ala Gly Lys Leu Thr Ala Ala Gly Ala Ser
225                 230                 235                 240

Leu Leu Asp Gln Ser Gly Thr Leu Asp Ala Gly Ser Val Ile Ala Pro
            245                 250                 255

Pro Glu Gly Asp Ala Gly Thr Gly Met Val Gly Thr Asn Ser Val Arg
                260                 265                 270

Lys Arg Thr Gly Asn Ile Ser Val Gly Thr Ser Ala Phe Ser Met Asn
            275                 280                 285

Val Leu Asp Lys Pro Leu Ser Lys Val Tyr Arg Asp Ile Asp Ile Val
            290                 295                 300

Met Thr Pro Asp Gly Ser Pro Val Ala Met Val His Val Asn Asn Cys
305                 310                 315                 320

Ser Ser Asp Ile Asn Ala Trp Ala Thr Ile Phe His Glu Phe Ala Ala
                325                 330                 335

Arg Leu Gly Met Glu Leu Lys Pro Asp Arg Leu Tyr Glu Thr Leu Phe
            340                 345                 350

Leu Glu Ser Thr Arg Ala Asp Ala Asp Ala Gly Gly Leu Ala Asn Tyr
            355                 360                 365

Ser Tyr Gln Ser Gly Glu Asn Ile Thr Lys Ile Gln Ala Gly Arg Pro
            370                 375                 380

Leu Phe Val Arg Thr Pro Asn Ser Lys Phe Ser Leu Pro Asn Phe Met
385                 390                 395                 400

Leu Thr Gln Leu Tyr Ala Ala Phe Ala Pro Leu Gln Leu Gly Met Asp
                405                 410                 415

Ile Leu Val Asn Glu Glu His Val Gln Thr Asp Val Met Ile Ala Gln
            420                 425                 430

Gly Gly Leu Phe Arg Thr Pro Val Ile Gly Gln Gln Val Leu Ala Asn
```

```
                          435                 440                 445
         Ala Leu Asn Ile Pro Ile Thr Val Met Ser Thr Ala Gly Glu Gly Gly
             450                 455                 460

Pro Trp Gly Met Ala Val Leu Ala Asn Phe Ala Cys Arg Gln Thr Ala
         465                 470                 475                 480

Met Asn Leu Glu Asp Phe Leu Asp Gln Glu Val Phe Lys Glu Pro Glu
                         485                 490                 495

Ser Met Thr Leu Ser Pro Glu Pro Glu Arg Val Ala Gly Tyr Arg Glu
                     500                 505                 510

Phe Ile Gln Arg Tyr Gln Ala Gly Leu Pro Val Glu Ala Ala Ala Gly
                     515                 520                 525

Gln Ala Ile Lys Tyr
             530

<210> SEQ ID NO 11
<211> LENGTH: 729
<212> TYPE: DNA
<213> ORGANISM: Lactobacillus plantarum
<220> FEATURE:
<221> NAME/KEY: CDS
<222> LOCATION: (1)..(729)

<400> SEQUENCE: 11
```

| | | | | | | | | | | | | | | | | |
|---|---|---|---|---|---|---|---|---|---|---|---|---|---|---|---|---|
| atg | ttg | gaa | gca | ttg | aag | caa | gaa | gtt | tac | gaa | gct | aac | atg | caa | ttg | 48 |
| Met | Leu | Glu | Ala | Leu | Lys | Gln | Glu | Val | Tyr | Glu | Ala | Asn | Met | Gln | Leu | |
| 1 | | | | 5 | | | | | 10 | | | | | 15 | | |
| cca | aag | ttg | ggt | tta | gtc | acc | ttt | act | tgg | ggt | aac | gta | tcc | ggt | atc | 96 |
| Pro | Lys | Leu | Gly | Leu | Val | Thr | Phe | Thr | Trp | Gly | Asn | Val | Ser | Gly | Ile | |
| | | 20 | | | | | 25 | | | | | 30 | | | | |
| gat | aga | gaa | aaa | ggt | ttg | ttc | gta | att | aag | cca | tcc | ggt | gtt | gac | tac | 144 |
| Asp | Arg | Glu | Lys | Gly | Leu | Phe | Val | Ile | Lys | Pro | Ser | Gly | Val | Asp | Tyr | |
| | | | 35 | | | | | 40 | | | | | 45 | | | |
| ggt | gaa | ttg | aaa | cct | agt | gat | ttg | gtt | gtc | gta | aat | ttg | caa | ggt | gaa | 192 |
| Gly | Glu | Leu | Lys | Pro | Ser | Asp | Leu | Val | Val | Val | Asn | Leu | Gln | Gly | Glu | |
| | 50 | | | | | 55 | | | | | 60 | | | | | |
| gtt | gtc | gag | ggt | aaa | tta | aac | cca | tct | tca | gac | aca | cct | acc | cat | act | 240 |
| Val | Val | Glu | Gly | Lys | Leu | Asn | Pro | Ser | Ser | Asp | Thr | Pro | Thr | His | Thr | |
| 65 | | | | | 70 | | | | | 75 | | | | | 80 | |
| gtt | ttg | tac | aac | gct | ttc | cca | aac | att | ggt | ggt | ata | gtt | cat | aca | cac | 288 |
| Val | Leu | Tyr | Asn | Ala | Phe | Pro | Asn | Ile | Gly | Gly | Ile | Val | His | Thr | His | |
| | | | | 85 | | | | | 90 | | | | | 95 | | |
| tct | cct | tgg | gcc | gtc | gct | tac | gct | gca | gcc | caa | atg | gat | gtt | cca | gct | 336 |
| Ser | Pro | Trp | Ala | Val | Ala | Tyr | Ala | Ala | Ala | Gln | Met | Asp | Val | Pro | Ala | |
| | | | 100 | | | | | 105 | | | | | 110 | | | |
| atg | aat | act | aca | cat | gca | gat | acc | ttc | tat | ggt | gac | gtt | cct | gct | gca | 384 |
| Met | Asn | Thr | Thr | His | Ala | Asp | Thr | Phe | Tyr | Gly | Asp | Val | Pro | Ala | Ala | |
| | | 115 | | | | | 120 | | | | | 125 | | | | |
| gat | gca | ttg | act | aaa | gaa | gaa | atc | gaa | gct | gac | tac | gag | ggt | aac | aca | 432 |
| Asp | Ala | Leu | Thr | Lys | Glu | Glu | Ile | Glu | Ala | Asp | Tyr | Glu | Gly | Asn | Thr | |
| | 130 | | | | | 135 | | | | | 140 | | | | | |
| ggt | aaa | acc | atc | gtt | aag | aca | ttc | caa | gaa | aga | ggt | ttg | gat | tac | gaa | 480 |
| Gly | Lys | Thr | Ile | Val | Lys | Thr | Phe | Gln | Glu | Arg | Gly | Leu | Asp | Tyr | Glu | |
| 145 | | | | | 150 | | | | | 155 | | | | | 160 | |
| gcc | gtc | cca | gct | tct | ttg | gta | tca | caa | cat | ggt | cct | ttc | gct | tgg | ggt | 528 |
| Ala | Val | Pro | Ala | Ser | Leu | Val | Ser | Gln | His | Gly | Pro | Phe | Ala | Trp | Gly | |
| | | | | 165 | | | | | 170 | | | | | 175 | | |
| cca | acc | cct | gca | aaa | gcc | gtt | tat | aat | gca | aag | gtc | tta | gaa | gta | gtt | 576 |
| Pro | Thr | Pro | Ala | Lys | Ala | Val | Tyr | Asn | Ala | Lys | Val | Leu | Glu | Val | Val | |
| | | | 180 | | | | | 185 | | | | | 190 | | | |

```
gcc gaa gaa gac tac cac act gca caa tta aca aga gcc tcc agt gaa    624
Ala Glu Glu Asp Tyr His Thr Ala Gln Leu Thr Arg Ala Ser Ser Glu
        195                 200                 205 ttg cca caa tat ttg ttg gat aag cat tac ttg aga aag cac ggt gct    672
Leu Pro Gln Tyr Leu Leu Asp Lys His Tyr Leu Arg Lys His Gly Ala
210                 215                 220 tct gca tat tac ggt caa aat aac gcc cat tca aaa gat cac gct gtt    720
Ser Ala Tyr Tyr Gly Gln Asn Asn Ala His Ser Lys Asp His Ala Val
225                 230                 235                 240 aga aag taa                                                        729
Arg Lys
```

<210> SEQ ID NO 12
<211> LENGTH: 242
<212> TYPE: PRT
<213> ORGANISM: Lactobacillus plantarum

<400> SEQUENCE: 12

```
Met Leu Glu Ala Leu Lys Gln Glu Val Tyr Glu Ala Asn Met Gln Leu
1               5                   10                  15

Pro Lys Leu Gly Leu Val Thr Phe Thr Trp Gly Asn Val Ser Gly Ile
            20                  25                  30

Asp Arg Glu Lys Gly Leu Phe Val Ile Lys Pro Ser Gly Val Asp Tyr
        35                  40                  45

Gly Glu Leu Lys Pro Ser Asp Leu Val Val Asn Leu Gln Gly Glu
    50                  55                  60

Val Val Glu Gly Lys Leu Asn Pro Ser Ser Asp Thr Pro Thr His Thr
65                  70                  75                  80

Val Leu Tyr Asn Ala Phe Pro Asn Ile Gly Gly Ile Val His Thr His
                85                  90                  95

Ser Pro Trp Ala Val Ala Tyr Ala Ala Gln Met Asp Val Pro Ala
            100                 105                 110

Met Asn Thr Thr His Ala Asp Thr Phe Tyr Gly Asp Val Pro Ala Ala
        115                 120                 125

Asp Ala Leu Thr Lys Glu Glu Ile Glu Ala Asp Tyr Glu Gly Asn Thr
    130                 135                 140

Gly Lys Thr Ile Val Lys Thr Phe Gln Glu Arg Gly Leu Asp Tyr Glu
145                 150                 155                 160

Ala Val Pro Ala Ser Leu Val Ser Gln His Gly Pro Phe Ala Trp Gly
                165                 170                 175

Pro Thr Pro Ala Lys Ala Val Tyr Asn Ala Lys Val Leu Glu Val Val
            180                 185                 190

Ala Glu Glu Asp Tyr His Thr Ala Gln Leu Thr Arg Ala Ser Ser Glu
        195                 200                 205

Leu Pro Gln Tyr Leu Leu Asp Lys His Tyr Leu Arg Lys His Gly Ala
    210                 215                 220

Ser Ala Tyr Tyr Gly Gln Asn Asn Ala His Ser Lys Asp His Ala Val
225                 230                 235                 240

Arg Lys
```

<210> SEQ ID NO 13
<211> LENGTH: 21
<212> TYPE: DNA
<213> ORGANISM: Artificial
<220> FEATURE:
<223> OTHER INFORMATION: synthetic DNA

<400> SEQUENCE: 13

```
tgggaatatt accgctcgaa g                                              21

<210> SEQ ID NO 14
<211> LENGTH: 29
<212> TYPE: DNA
<213> ORGANISM: Artificial
<220> FEATURE:
<223> OTHER INFORMATION: synthetic DNA

<400> SEQUENCE: 14
ctttaaaaaa tttccaattt tcctttacg                                      29

<210> SEQ ID NO 15
<211> LENGTH: 33
<212> TYPE: DNA
<213> ORGANISM: Artificial
<220> FEATURE:
<223> OTHER INFORMATION: synthetic DNA

<400> SEQUENCE: 15
ggaaattttt taaagtcgca gccacgggtc aac                                 33

<210> SEQ ID NO 16
<211> LENGTH: 50
<212> TYPE: DNA
<213> ORGANISM: Artificial
<220> FEATURE:
<223> OTHER INFORMATION: synthetic DNA

<400> SEQUENCE: 16
gtgaattgag tcattttta ttattagtct ttttttttt tgacaatatc                 50

<210> SEQ ID NO 17
<211> LENGTH: 31
<212> TYPE: DNA
<213> ORGANISM: Artificial
<220> FEATURE:
<223> OTHER INFORMATION: synthetic DNA

<400> SEQUENCE: 17
atgactcaat tcactgacat tgataagcta g                                   31

<210> SEQ ID NO 18
<211> LENGTH: 37
<212> TYPE: DNA
<213> ORGANISM: Artificial
<220> FEATURE:
<223> OTHER INFORMATION: synthetic DNA

<400> SEQUENCE: 18
ccttaaatca acgtcatatt ctttattggc tttatac                             37

<210> SEQ ID NO 19
<211> LENGTH: 24
<212> TYPE: DNA
<213> ORGANISM: Artificial
<220> FEATURE:
<223> OTHER INFORMATION: synthetic DNA

<400> SEQUENCE: 19
gacgttgatt taaggtggtt ccgg                                           24

<210> SEQ ID NO 20
<211> LENGTH: 25
<212> TYPE: DNA
```

<213> ORGANISM: Artificial
<220> FEATURE:
<223> OTHER INFORMATION: synthetic DNA

<400> SEQUENCE: 20
atgtctgaac cagctcaaaa gaaac                                  25

<210> SEQ ID NO 21
<211> LENGTH: 52
<212> TYPE: DNA
<213> ORGANISM: Artificial
<220> FEATURE:
<223> OTHER INFORMATION: synthetic DNA

<400> SEQUENCE: 21
agctggttca gacattttga atatgtatta cttggttatg gttatatatg ac    52

<210> SEQ ID NO 22
<211> LENGTH: 41
<212> TYPE: DNA
<213> ORGANISM: Artificial
<220> FEATURE:
<223> OTHER INFORMATION: synthetic DNA

<400> SEQUENCE: 22
cacccaaatg aattgaaagc gactggtaga gagcgacttt g                41

<210> SEQ ID NO 23
<211> LENGTH: 22
<212> TYPE: DNA
<213> ORGANISM: Artificial
<220> FEATURE:
<223> OTHER INFORMATION: synthetic DNA

<400> SEQUENCE: 23
gctttcaatt catttgggtg tg                                     22

<210> SEQ ID NO 24
<211> LENGTH: 30
<212> TYPE: DNA
<213> ORGANISM: Artificial
<220> FEATURE:
<223> OTHER INFORMATION: synthetic DNA

<400> SEQUENCE: 24
tgtatatgag atagttgatt gtatgcttgg                             30

<210> SEQ ID NO 25
<211> LENGTH: 39
<212> TYPE: DNA
<213> ORGANISM: Artificial
<220> FEATURE:
<223> OTHER INFORMATION: synthetic DNA

<400> SEQUENCE: 25
actatctcat atacaatggt caaaccaatt atagctccc                   39

<210> SEQ ID NO 26
<211> LENGTH: 25
<212> TYPE: DNA
<213> ORGANISM: Artificial
<220> FEATURE:
<223> OTHER INFORMATION: synthetic DNA

<400> SEQUENCE: 26
aaatggatat tgatctagat ggcgg                                  25

```
<210> SEQ ID NO 27
<211> LENGTH: 41
<212> TYPE: DNA
<213> ORGANISM: Artificial
<220> FEATURE:
<223> OTHER INFORMATION: synthetic DNA

<400> SEQUENCE: 27
gatcaatatc catttcttgg tgtgtcatcg gtagtaacgc c                    41

<210> SEQ ID NO 28
<211> LENGTH: 35
<212> TYPE: DNA
<213> ORGANISM: Artificial
<220> FEATURE:
<223> OTHER INFORMATION: synthetic DNA

<400> SEQUENCE: 28
agttttaatt acaaaatggc tgccggtgtc ccaaa                           35

<210> SEQ ID NO 29
<211> LENGTH: 36
<212> TYPE: DNA
<213> ORGANISM: Artificial
<220> FEATURE:
<223> OTHER INFORMATION: synthetic DNA

<400> SEQUENCE: 29
ttgtaattaa aacttagatt agattgctat gctttc                          36

<210> SEQ ID NO 30
<211> LENGTH: 18
<212> TYPE: DNA
<213> ORGANISM: Artificial
<220> FEATURE:
<223> OTHER INFORMATION: synthetic DNA

<400> SEQUENCE: 30
aggaacagcc gtcaaggg                                              18

<210> SEQ ID NO 31
<211> LENGTH: 35
<212> TYPE: DNA
<213> ORGANISM: Artificial
<220> FEATURE:
<223> OTHER INFORMATION: synthetic DNA

<400> SEQUENCE: 31
ttgacggctg ttcctcttcc cttttacagt gcttc                           35

<210> SEQ ID NO 32
<211> LENGTH: 42
<212> TYPE: DNA
<213> ORGANISM: Artificial
<220> FEATURE:
<223> OTHER INFORMATION: synthetic DNA

<400> SEQUENCE: 32
aaaaatttga gacattttgt tttgtgtgta aatttagtga ag                   42

<210> SEQ ID NO 33
<211> LENGTH: 28
<212> TYPE: DNA
<213> ORGANISM: Artificial
<220> FEATURE:
```

<223> OTHER INFORMATION: synthetic DNA

<400> SEQUENCE: 33
atgtctcaaa ttttttaagga tatcccag                                    28

<210> SEQ ID NO 34
<211> LENGTH: 50
<212> TYPE: DNA
<213> ORGANISM: Artificial
<220> FEATURE:
<223> OTHER INFORMATION: synthetic DNA

<400> SEQUENCE: 34
agcgctctta ctttagcgat cgcactagtt tattgaaaca aaatttggtt              50

<210> SEQ ID NO 35
<211> LENGTH: 28
<212> TYPE: DNA
<213> ORGANISM: Artificial
<220> FEATURE:
<223> OTHER INFORMATION: synthetic DNA

<400> SEQUENCE: 35
taaagtaaga gcgctacatt ggtctacc                                     28

<210> SEQ ID NO 36
<211> LENGTH: 36
<212> TYPE: DNA
<213> ORGANISM: Artificial
<220> FEATURE:
<223> OTHER INFORMATION: synthetic DNA

<400> SEQUENCE: 36
taacattcaa cgctattact ccgcaacgct tttctg                            36

<210> SEQ ID NO 37
<211> LENGTH: 26
<212> TYPE: DNA
<213> ORGANISM: Artificial
<220> FEATURE:
<223> OTHER INFORMATION: synthetic DNA

<400> SEQUENCE: 37
tagcgttgaa tgttagcgtc aacaac                                       26

<210> SEQ ID NO 38
<211> LENGTH: 41
<212> TYPE: DNA
<213> ORGANISM: Artificial
<220> FEATURE:
<223> OTHER INFORMATION: synthetic DNA

<400> SEQUENCE: 38
tactgaacac aacatttttgt ttgtttatgt gtgtttattc g                      41

<210> SEQ ID NO 39
<211> LENGTH: 27
<212> TYPE: DNA
<213> ORGANISM: Artificial
<220> FEATURE:
<223> OTHER INFORMATION: synthetic DNA

<400> SEQUENCE: 39
atgttgtgtt cagtaattca gagacag                                      27

```
<210> SEQ ID NO 40
<211> LENGTH: 39
<212> TYPE: DNA
<213> ORGANISM: Artificial
<220> FEATURE:
<223> OTHER INFORMATION: synthetic DNA

<400> SEQUENCE: 40
aaataatcgg tgtcattaga tgagagtctt ttccagttc                          39

<210> SEQ ID NO 41
<211> LENGTH: 25
<212> TYPE: DNA
<213> ORGANISM: Artificial
<220> FEATURE:
<223> OTHER INFORMATION: synthetic DNA

<400> SEQUENCE: 41
tgacaccgat tatttaaagc tgcag                                         25

<210> SEQ ID NO 42
<211> LENGTH: 70
<212> TYPE: DNA
<213> ORGANISM: Artificial
<220> FEATURE:
<223> OTHER INFORMATION: synthetic DNA

<400> SEQUENCE: 42
ataatgtatg ctatacgaag ttatagggaa agatatgagc tatacagcgg aattagagcg   60
cgcctcgttc                                                          70

<210> SEQ ID NO 43
<211> LENGTH: 43
<212> TYPE: DNA
<213> ORGANISM: Artificial
<220> FEATURE:
<223> OTHER INFORMATION: synthetic DNA

<400> SEQUENCE: 43
tatagcatac attatacgaa gttatacgac atcgtcgaat atg                     43

<210> SEQ ID NO 44
<211> LENGTH: 48
<212> TYPE: DNA
<213> ORGANISM: Artificial
<220> FEATURE:
<223> OTHER INFORMATION: synthetic DNA

<400> SEQUENCE: 44
ttgaatatgg ctcattatta atttagtgtg tgtatttgtg tttgtgtg                48

<210> SEQ ID NO 45
<211> LENGTH: 23
<212> TYPE: DNA
<213> ORGANISM: Artificial
<220> FEATURE:
<223> OTHER INFORMATION: synthetic DNA

<400> SEQUENCE: 45
atgagccata ttcaacggga aac                                           23

<210> SEQ ID NO 46
<211> LENGTH: 38
<212> TYPE: DNA
<213> ORGANISM: Artificial
<220> FEATURE:
```

<223> OTHER INFORMATION: synthetic DNA

<400> SEQUENCE: 46
tttagtagac atgcattaca accaattaac caattctg                    38

<210> SEQ ID NO 47
<211> LENGTH: 37
<212> TYPE: DNA
<213> ORGANISM: Artificial
<220> FEATURE:
<223> OTHER INFORMATION: synthetic DNA

<400> SEQUENCE: 47
tgcatgtcta ctaaactcac aaattagagc ttcaatt                    37

<210> SEQ ID NO 48
<211> LENGTH: 54
<212> TYPE: DNA
<213> ORGANISM: Artificial
<220> FEATURE:
<223> OTHER INFORMATION: synthetic DNA

<400> SEQUENCE: 48
ataatgtatg ctatacgaag ttatgggtaa taactgatat aattaaattg aagc        54

<210> SEQ ID NO 49
<211> LENGTH: 81
<212> TYPE: DNA
<213> ORGANISM: Artificial
<220> FEATURE:
<223> OTHER INFORMATION: synthetic DNA

<400> SEQUENCE: 49
tatagcatac attatacgaa gttattgaca ccgattattt aaagctgcag catactccag    60
ccagtaaaat ccatactcaa c                                     81

<210> SEQ ID NO 50
<211> LENGTH: 20
<212> TYPE: DNA
<213> ORGANISM: Artificial
<220> FEATURE:
<223> OTHER INFORMATION: synthetic DNA

<400> SEQUENCE: 50 gtcttttgc cagccagtcc                                        20

<210> SEQ ID NO 51
<211> LENGTH: 35
<212> TYPE: DNA
<213> ORGANISM: Artificial
<220> FEATURE:
<223> OTHER INFORMATION: synthetic DNA

<400> SEQUENCE: 51
ggctggcaaa aagacggccc tgcattaatg aatcg                      35

<210> SEQ ID NO 52
<211> LENGTH: 35
<212> TYPE: DNA
<213> ORGANISM: Artificial
<220> FEATURE:
<223> OTHER INFORMATION: synthetic DNA

<400> SEQUENCE: 52
gcggtaatat tcccaactag tggatcatcc ccacg                      35

<210> SEQ ID NO 53
<211> LENGTH: 44
<212> TYPE: DNA
<213> ORGANISM: Artificial
<220> FEATURE:
<223> OTHER INFORMATION: synthetic DNA

<400> SEQUENCE: 53
acggccagtg aattcggctg atgtaatggt attgttattc aacc        44

<210> SEQ ID NO 54
<211> LENGTH: 43
<212> TYPE: DNA
<213> ORGANISM: Artificial
<220> FEATURE:
<223> OTHER INFORMATION: synthetic DNA

<400> SEQUENCE: 54
gcagatgcat ggatcgtttt taccagcatc agcgcctagg aac         43

<210> SEQ ID NO 55
<211> LENGTH: 19
<212> TYPE: DNA
<213> ORGANISM: Artificial
<220> FEATURE:
<223> OTHER INFORMATION: synthetic DNA

<400> SEQUENCE: 55
aacgatccat gcatctgcc                                    19

<210> SEQ ID NO 56
<211> LENGTH: 46
<212> TYPE: DNA
<213> ORGANISM: Artificial
<220> FEATURE:
<223> OTHER INFORMATION: synthetic DNA

<400> SEQUENCE: 56
cttaatagag cgaacgtatt ttattttgct tgtctttgta gttacg      46

<210> SEQ ID NO 57
<211> LENGTH: 42
<212> TYPE: DNA
<213> ORGANISM: Artificial
<220> FEATURE:
<223> OTHER INFORMATION: synthetic DNA

<400> SEQUENCE: 57
tacgttcgct ctattaagat ggcagttgag gagaacaata tg          42

<210> SEQ ID NO 58
<211> LENGTH: 41
<212> TYPE: DNA
<213> ORGANISM: Artificial
<220> FEATURE:
<223> OTHER INFORMATION: synthetic DNA

<400> SEQUENCE: 58
tattttccat caaccagctt attctagcat ggccttgtac c           41

<210> SEQ ID NO 59
<211> LENGTH: 30
<212> TYPE: DNA
<213> ORGANISM: Artificial
<220> FEATURE:

<223> OTHER INFORMATION: synthetic DNA

<400> SEQUENCE: 59
gctggttgat ggaaaatata attttattgg                                            30

<210> SEQ ID NO 60
<211> LENGTH: 24
<212> TYPE: DNA
<213> ORGANISM: Artificial
<220> FEATURE:
<223> OTHER INFORMATION: synthetic DNA

<400> SEQUENCE: 60
ggaaaaacgg gaagaaaagg aaag                                                  24

<210> SEQ ID NO 61
<211> LENGTH: 38
<212> TYPE: DNA
<213> ORGANISM: Artificial
<220> FEATURE:
<223> OTHER INFORMATION: synthetic DNA

<400> SEQUENCE: 61
ttttcttccc gttttcctta gcgttgaatg ttagcgtc                                   38

<210> SEQ ID NO 62
<211> LENGTH: 29
<212> TYPE: DNA
<213> ORGANISM: Artificial
<220> FEATURE:
<223> OTHER INFORMATION: synthetic DNA

<400> SEQUENCE: 62
cattttgttt gtttatgtgt gtttattcg                                             29

<210> SEQ ID NO 63
<211> LENGTH: 35
<212> TYPE: DNA
<213> ORGANISM: Artificial
<220> FEATURE:
<223> OTHER INFORMATION: synthetic DNA

<400> SEQUENCE: 63
acataaacaa acaaaatgaa tttggtcgaa accgc                                      35

<210> SEQ ID NO 64
<211> LENGTH: 42
<212> TYPE: DNA
<213> ORGANISM: Artificial
<220> FEATURE:
<223> OTHER INFORMATION: synthetic DNA

<400> SEQUENCE: 64
agcgctctta ctttattagt atttaatagc ttgaccagcg gc                              42

<210> SEQ ID NO 65
<211> LENGTH: 28
<212> TYPE: DNA
<213> ORGANISM: Artificial
<220> FEATURE:
<223> OTHER INFORMATION: synthetic DNA

<400> SEQUENCE: 65
taaagtaaga gcgctacatt ggtctacc                                              28

```
<210> SEQ ID NO 66
<211> LENGTH: 24
<212> TYPE: DNA
<213> ORGANISM: Artificial
<220> FEATURE:
<223> OTHER INFORMATION: synthetic DNA

<400> SEQUENCE: 66
ttactccgca acgcttttct gaac                                          24

<210> SEQ ID NO 67
<211> LENGTH: 33
<212> TYPE: DNA
<213> ORGANISM: Artificial
<220> FEATURE:
<223> OTHER INFORMATION: synthetic DNA

<400> SEQUENCE: 67
agcgttgcgg agtaatcgca gccacgggtc aac                                33

<210> SEQ ID NO 68
<211> LENGTH: 47
<212> TYPE: DNA
<213> ORGANISM: Artificial
<220> FEATURE:
<223> OTHER INFORMATION: synthetic DNA

<400> SEQUENCE: 68
tttttattat tagtcttttt tttttttgac aatatctgta tgatttg                 47

<210> SEQ ID NO 69
<211> LENGTH: 44
<212> TYPE: DNA
<213> ORGANISM: Artificial
<220> FEATURE:
<223> OTHER INFORMATION: synthetic DNA

<400> SEQUENCE: 69
agactaataa taaaaatgtt gtccgttcca gattatgaat tttg                    44

<210> SEQ ID NO 70
<211> LENGTH: 45
<212> TYPE: DNA
<213> ORGANISM: Artificial
<220> FEATURE:
<223> OTHER INFORMATION: synthetic DNA

<400> SEQUENCE: 70
ttgctctcaa tccgcttatt ttaagaaagc ctttgtcata ccaac                   45

<210> SEQ ID NO 71
<211> LENGTH: 25
<212> TYPE: DNA
<213> ORGANISM: Artificial
<220> FEATURE:
<223> OTHER INFORMATION: synthetic DNA

<400> SEQUENCE: 71
gcggattgag agcaaatcgt taagt                                         25

<210> SEQ ID NO 72
<211> LENGTH: 22
<212> TYPE: DNA
<213> ORGANISM: Artificial
<220> FEATURE:
<223> OTHER INFORMATION: synthetic DNA
```

<400> SEQUENCE: 72
agaggcatag cggcaaacta ag                                              22

<210> SEQ ID NO 73
<211> LENGTH: 33
<212> TYPE: DNA
<213> ORGANISM: Artificial
<220> FEATURE:
<223> OTHER INFORMATION: synthetic DNA

<400> SEQUENCE: 73
tgccgctatg cctctaaaca agctcccaag ggc                                  33

<210> SEQ ID NO 74
<211> LENGTH: 42
<212> TYPE: DNA
<213> ORGANISM: Artificial
<220> FEATURE:
<223> OTHER INFORMATION: synthetic DNA

<400> SEQUENCE: 74
gaagttttgt tagaaaataa atcatttttt aattgagcat tc                        42

<210> SEQ ID NO 75
<211> LENGTH: 44
<212> TYPE: DNA
<213> ORGANISM: Artificial
<220> FEATURE:
<223> OTHER INFORMATION: synthetic DNA

<400> SEQUENCE: 75
attttctaac aaaacttctt actttctaac agcgtgatct tttg                      44

<210> SEQ ID NO 76
<211> LENGTH: 43
<212> TYPE: DNA
<213> ORGANISM: Artificial
<220> FEATURE:
<223> OTHER INFORMATION: synthetic DNA

<400> SEQUENCE: 76
aagtaataca tattcaaaat gttggaagca ttgaagcaag aag                       43

<210> SEQ ID NO 77
<211> LENGTH: 44
<212> TYPE: DNA
<213> ORGANISM: Artificial
<220> FEATURE:
<223> OTHER INFORMATION: synthetic DNA

<400> SEQUENCE: 77
cattttgaat atgtattact tggttatggt tatatatgac aaaa                      44

<210> SEQ ID NO 78
<211> LENGTH: 79
<212> TYPE: DNA
<213> ORGANISM: Artificial
<220> FEATURE:
<223> OTHER INFORMATION: synthetic DNA

<400> SEQUENCE: 78
atagcataca ttatacgaac ggtatgacac cgattattta aagctgcagc atacactggt     60
agagagcgac tttgtatgc                                                  79

```
<210> SEQ ID NO 79
<211> LENGTH: 64
<212> TYPE: DNA
<213> ORGANISM: Artificial
<220> FEATURE:
<223> OTHER INFORMATION: synthetic DNA

<400> SEQUENCE: 79
tataatgtat gctatacgaa gttatagctt gcaaattaaa gccttcgagc gtcccaaaac    60
cttc                                                                64

<210> SEQ ID NO 80
<211> LENGTH: 26
<212> TYPE: DNA
<213> ORGANISM: Artificial
<220> FEATURE:
<223> OTHER INFORMATION: synthetic DNA

<400> SEQUENCE: 80
ttagttatgt cacgcttaca ttcacg                                         26

<210> SEQ ID NO 81
<211> LENGTH: 25
<212> TYPE: DNA
<213> ORGANISM: Artificial
<220> FEATURE:
<223> OTHER INFORMATION: synthetic DNA

<400> SEQUENCE: 81
gctttcgaaa gaactgattt cgatc                                          25

<210> SEQ ID NO 82
<211> LENGTH: 38
<212> TYPE: DNA
<213> ORGANISM: Artificial
<220> FEATURE:
<223> OTHER INFORMATION: synthetic DNA

<400> SEQUENCE: 82
gcgtgacata actaatcaat caccatcttc caacaatc                            38

<210> SEQ ID NO 83
<211> LENGTH: 67
<212> TYPE: DNA
<213> ORGANISM: Artificial
<220> FEATURE:
<223> OTHER INFORMATION: synthetic DNA

<400> SEQUENCE: 83
gctaagcagg ctttggcatg tataacaaac actgattttt gttttgagtt ttaaaagata    60
tccattt                                                              67

<210> SEQ ID NO 84
<211> LENGTH: 66
<212> TYPE: DNA
<213> ORGANISM: Artificial
<220> FEATURE:
<223> OTHER INFORMATION: synthetic DNA

<400> SEQUENCE: 84
agttctttcg aaagcctgca aaacttgtgc ttgtacacct cgaatgttag taaatggata    60
tctttt                                                               66

<210> SEQ ID NO 85
```

<210> SEQ ID NO 85
<211> LENGTH: 37
<212> TYPE: DNA
<213> ORGANISM: Artificial
<220> FEATURE:
<223> OTHER INFORMATION: synthetic DNA

<400> SEQUENCE: 85
caaggagaaa aaaccatgtc taacttgttg actgttc 37

<210> SEQ ID NO 86
<211> LENGTH: 23
<212> TYPE: DNA
<213> ORGANISM: Artificial
<220> FEATURE:
<223> OTHER INFORMATION: synthetic DNA

<400> SEQUENCE: 86
caaagcctgc ttagctcttt cac 23

<210> SEQ ID NO 87
<211> LENGTH: 76
<212> TYPE: DNA
<213> ORGANISM: Artificial
<220> FEATURE:
<223> OTHER INFORMATION: synthetic DNA

<400> SEQUENCE: 87
tgcatgtcta ctaaactcac aaattagagc ttcaatttaa ttatatcagt tattacccac 60
ggattagaag ccgccg 76

<210> SEQ ID NO 88
<211> LENGTH: 29
<212> TYPE: DNA
<213> ORGANISM: Artificial
<220> FEATURE:
<223> OTHER INFORMATION: synthetic DNA

<400> SEQUENCE: 88
ggttttttct ccttgacgtt aaagtatag 29

<210> SEQ ID NO 89
<211> LENGTH: 35
<212> TYPE: DNA
<213> ORGANISM: Artificial
<220> FEATURE:
<223> OTHER INFORMATION: synthetic DNA

<400> SEQUENCE: 89
tttagtagac atgcattagc cctcccacac ataac 35

<210> SEQ ID NO 90
<211> LENGTH: 48
<212> TYPE: DNA
<213> ORGANISM: Artificial
<220> FEATURE:
<223> OTHER INFORMATION: synthetic DNA

<400> SEQUENCE: 90
atagcataca ttatacgaag ttatcccaca caccatagct tcaaaatg 48

<210> SEQ ID NO 91
<211> LENGTH: 48
<212> TYPE: DNA
<213> ORGANISM: Artificial
<220> FEATURE:
<223> OTHER INFORMATION: synthetic DNA

<400> SEQUENCE: 91
atagcataca ttatacgaag ttatcccaca caccatagct tcaaaatg        48

<210> SEQ ID NO 92
<211> LENGTH: 39
<212> TYPE: DNA
<213> ORGANISM: Artificial
<220> FEATURE:
<223> OTHER INFORMATION: synthetic DNA

<400> SEQUENCE: 92
tccccgggta ccgagtattc cttgttttgt tcagcctgg               39

<210> SEQ ID NO 93
<211> LENGTH: 19
<212> TYPE: DNA
<213> ORGANISM: Artificial
<220> FEATURE:
<223> OTHER INFORMATION: synthetic DNA

<400> SEQUENCE: 93
atttagcatc gtgcatggg                                       19

<210> SEQ ID NO 94
<211> LENGTH: 41
<212> TYPE: DNA
<213> ORGANISM: Artificial
<220> FEATURE:
<223> OTHER INFORMATION: synthetic DNA

<400> SEQUENCE: 94
taacattcaa cgctaattcc atagcttagt ttaatcaagg c             41

<210> SEQ ID NO 95
<211> LENGTH: 26
<212> TYPE: DNA
<213> ORGANISM: Artificial
<220> FEATURE:
<223> OTHER INFORMATION: synthetic DNA

<400> SEQUENCE: 95
tagcgttgaa tgttagcgtc aacaac                              26

<210> SEQ ID NO 96
<211> LENGTH: 29
<212> TYPE: DNA
<213> ORGANISM: Artificial
<220> FEATURE:
<223> OTHER INFORMATION: synthetic DNA

<400> SEQUENCE: 96
cattttgttt gtttatgtgt gtttattcg                           29

<210> SEQ ID NO 97
<211> LENGTH: 35
<212> TYPE: DNA
<213> ORGANISM: Artificial
<220> FEATURE:
<223> OTHER INFORMATION: synthetic DNA

<400> SEQUENCE: 97
acataaacaa acaaaatgat tggtcctcgt ctttg                    35

<210> SEQ ID NO 98

```
<211> LENGTH: 37
<212> TYPE: DNA
<213> ORGANISM: Artificial
<220> FEATURE:
<223> OTHER INFORMATION: synthetic DNA

<400> SEQUENCE: 98
ttgctctcaa tccgcctatg gatgaatgtc ggtcaag                              37

<210> SEQ ID NO 99
<211> LENGTH: 25
<212> TYPE: DNA
<213> ORGANISM: Artificial
<220> FEATURE:
<223> OTHER INFORMATION: synthetic DNA

<400> SEQUENCE: 99
gcggattgag agcaaatcgt taagt                                           25

<210> SEQ ID NO 100
<211> LENGTH: 76
<212> TYPE: DNA
<213> ORGANISM: Artificial
<220> FEATURE:
<223> OTHER INFORMATION: synthetic DNA

<400> SEQUENCE: 100
ataatgtatg ctatacgaac ggtaagggaa agatatgagc tatacagcgg aattagaggc     60
atagcggcaa actaag                                                     76

<210> SEQ ID NO 101
<211> LENGTH: 48
<212> TYPE: DNA
<213> ORGANISM: Artificial
<220> FEATURE:
<223> OTHER INFORMATION: synthetic DNA

<400> SEQUENCE: 101
atagcataca ttatacgaag ttatcccaca caccatagct tcaaaatg                  48

<210> SEQ ID NO 102
<211> LENGTH: 37
<212> TYPE: DNA
<213> ORGANISM: Artificial
<220> FEATURE:
<223> OTHER INFORMATION: synthetic DNA

<400> SEQUENCE: 102
caccgaaatc ttcatccctt agattagatt gctatgc                              37

<210> SEQ ID NO 103
<211> LENGTH: 17
<212> TYPE: DNA
<213> ORGANISM: Artificial
<220> FEATURE:
<223> OTHER INFORMATION: synthetic DNA

<400> SEQUENCE: 103
atgaagattt cggtgat                                                    17

<210> SEQ ID NO 104
<211> LENGTH: 20
<212> TYPE: DNA
<213> ORGANISM: Artificial
<220> FEATURE:
<223> OTHER INFORMATION: synthetic DNA
```

<400> SEQUENCE: 104
ttaggcgtca tcctgtgctc                                                    20

<210> SEQ ID NO 105
<211> LENGTH: 45
<212> TYPE: DNA
<213> ORGANISM: Artificial
<220> FEATURE:
<223> OTHER INFORMATION: synthetic DNA

<400> SEQUENCE: 105
caggatgacg cctaaaaaga ttctcttttt ttatgatatt tgtac                        45

<210> SEQ ID NO 106
<211> LENGTH: 30
<212> TYPE: DNA
<213> ORGANISM: Artificial
<220> FEATURE:
<223> OTHER INFORMATION: synthetic DNA

<400> SEQUENCE: 106
aggaatcata gtttcatgat tttctgttac                                         30

<210> SEQ ID NO 107
<211> LENGTH: 33
<212> TYPE: DNA
<213> ORGANISM: Artificial
<220> FEATURE:
<223> OTHER INFORMATION: synthetic DNA

<400> SEQUENCE: 107
gaaactatga ttcctacgga ttagaagccg ccg                                     33

<210> SEQ ID NO 108
<211> LENGTH: 64
<212> TYPE: DNA
<213> ORGANISM: Artificial
<220> FEATURE:
<223> OTHER INFORMATION: synthetic DNA

<400> SEQUENCE: 108
tataatgtat gctatacgaa gttatagctt gcaaattaaa gccttcgagc gtcccaaaac        60
cttc                                                                    64

<210> SEQ ID NO 109
<211> LENGTH: 78
<212> TYPE: DNA
<213> ORGANISM: Artificial
<220> FEATURE:
<223> OTHER INFORMATION: synthetic DNA

<400> SEQUENCE: 109
atagcataca ttatacgaac ggtatgacac cgattattta aagctgcagc atacttgcat        60
tattcaagtt ttagggtg                                                     78

<210> SEQ ID NO 110
<211> LENGTH: 19
<212> TYPE: DNA
<213> ORGANISM: Artificial
<220> FEATURE:
<223> OTHER INFORMATION: synthetic DNA

<400> SEQUENCE: 110

```
cattctgtat gcgatgccc                                                  19
```

<210> SEQ ID NO 111
<211> LENGTH: 33
<212> TYPE: DNA
<213> ORGANISM: Artificial
<220> FEATURE:
<223> OTHER INFORMATION: synthetic DNA

<400> SEQUENCE: 111

```
atcgcataca gaatggatcc ccgggtaccg agc                                  33
```

<210> SEQ ID NO 112
<211> LENGTH: 36
<212> TYPE: DNA
<213> ORGANISM: Artificial
<220> FEATURE:
<223> OTHER INFORMATION: synthetic DNA

<400> SEQUENCE: 112

```
tgcacgatgc taaatgatcc tctagagtcg acctgc                               36
```

<210> SEQ ID NO 113
<211> LENGTH: 25
<212> TYPE: DNA
<213> ORGANISM: Artificial
<220> FEATURE:
<223> OTHER INFORMATION: synthetic DNA

<400> SEQUENCE: 113

```
gcggattgag agcaaatcgt taagt                                           25
```

<210> SEQ ID NO 114
<211> LENGTH: 55
<212> TYPE: DNA
<213> ORGANISM: Artificial
<220> FEATURE:
<223> OTHER INFORMATION: synthetic DNA

<400> SEQUENCE: 114

```
tttgtttgtt tatgtgtgtt tattcgaaac taagttcttg gtgttttaaa actaa          55
```

<210> SEQ ID NO 115
<211> LENGTH: 42
<212> TYPE: DNA
<213> ORGANISM: Artificial
<220> FEATURE:
<223> OTHER INFORMATION: synthetic DNA

<400> SEQUENCE: 115

```
cacacataaa caaacaaaat ggccgttgca caacgttggg gc                        42
```

<210> SEQ ID NO 116
<211> LENGTH: 37
<212> TYPE: DNA
<213> ORGANISM: Artificial
<220> FEATURE:
<223> OTHER INFORMATION: synthetic DNA

<400> SEQUENCE: 116

```
ttgctctcaa tccgcctatg gatgaatgtc ggtcaag                              37
```

<210> SEQ ID NO 117
<211> LENGTH: 25
<212> TYPE: DNA
<213> ORGANISM: Artificial

```
<220> FEATURE:
<223> OTHER INFORMATION: synthetic DNA

<400> SEQUENCE: 117
gcggattgag agcaaatcgt taagt                                     25

<210> SEQ ID NO 118
<211> LENGTH: 55
<212> TYPE: DNA
<213> ORGANISM: Artificial
<220> FEATURE:
<223> OTHER INFORMATION: synthetic DNA

<400> SEQUENCE: 118
tttgtttgtt tatgtgtgtt tattcgaaac taagttcttg gtgttttaaa actaa    55

<210> SEQ ID NO 119
<211> LENGTH: 43
<212> TYPE: DNA
<213> ORGANISM: Artificial
<220> FEATURE:
<223> OTHER INFORMATION: synthetic DNA

<400> SEQUENCE: 119
cacacataaa caaacaaaat ggaccgcatt attcaatcac cgg                 43

<210> SEQ ID NO 120
<211> LENGTH: 38
<212> TYPE: DNA
<213> ORGANISM: Artificial
<220> FEATURE:
<223> OTHER INFORMATION: synthetic DNA

<400> SEQUENCE: 120
ttgctctcaa tccgcttatt cccactcttg caggaaac                       38

<210> SEQ ID NO 121
<211> LENGTH: 25
<212> TYPE: DNA
<213> ORGANISM: Artificial
<220> FEATURE:
<223> OTHER INFORMATION: synthetic DNA

<400> SEQUENCE: 121
gcggattgag agcaaatcgt taagt                                     25

<210> SEQ ID NO 122
<211> LENGTH: 55
<212> TYPE: DNA
<213> ORGANISM: Artificial
<220> FEATURE:
<223> OTHER INFORMATION: synthetic DNA

<400> SEQUENCE: 122
tttgtttgtt tatgtgtgtt tattcgaaac taagttcttg gtgttttaaa actaa    55

<210> SEQ ID NO 123
<211> LENGTH: 35
<212> TYPE: DNA
<213> ORGANISM: Artificial
<220> FEATURE:
<223> OTHER INFORMATION: synthetic DNA

<400> SEQUENCE: 123
acataaacaa acaaaatgat tggtcctcgt ctttg                          35
```

```
<210> SEQ ID NO 124
<211> LENGTH: 41
<212> TYPE: DNA
<213> ORGANISM: Artificial
<220> FEATURE:
<223> OTHER INFORMATION: synthetic DNA

<400> SEQUENCE: 124
ttgaataatg cggtccatag aggcgagcgc aaatacttta g                41
```